US011356810B1

(12) United States Patent
Akpinar et al.

(10) Patent No.: US 11,356,810 B1
(45) Date of Patent: Jun. 7, 2022

(54) METHODS AND SYSTEMS OF REDUCING THE SPREAD OF CONTAGIONS

(71) Applicant: Pointr Limited, London (GB)

(72) Inventors: Ismail Ege Akpinar, Boston, MA (US); Mehmet Can Akpinar, Istanbul (TR); Can Tunca, Istanbul (TR); Guneykan Ozgul, Istanbul (TR); Sinan Isik, Istanbul (TR); Mehmet Bilgay Akhan, Hampshire (GB)

(73) Assignee: Pointr Limited, London (GB)

( * ) Notice: Subject to any disclaimer, the term of this patent is extended or adjusted under 35 U.S.C. 154(b) by 56 days.

(21) Appl. No.: 17/018,871

(22) Filed: Sep. 11, 2020

(51) Int. Cl.

| | |
|---|---|
| *H04W 4/029* | (2018.01) |
| *G16H 50/80* | (2018.01) |
| *H04W 4/021* | (2018.01) |
| *H04W 4/02* | (2018.01) |

(52) U.S. Cl.
CPC ............ *H04W 4/029* (2018.02); *G16H 50/80* (2018.01); *H04W 4/021* (2013.01); *H04W 4/026* (2013.01)

(58) Field of Classification Search
CPC ..... H04W 4/029; H04W 4/021; H04W 4/026; G16H 50/80
USPC ........................................................ 455/456.1
See application file for complete search history.

(56) References Cited

U.S. PATENT DOCUMENTS

| | | | | |
|---|---|---|---|---|
| 8,405,503 | B2 | 3/2013 | Wong | |
| 10,198,779 | B2 | 2/2019 | Pittman et al. | |
| 2021/0313075 | A1* | 10/2021 | Mc Namara ........... | G08B 21/22 |
| 2021/0390807 | A1* | 12/2021 | Chaurasia ............. | G16H 40/40 |

OTHER PUBLICATIONS

Work.com "Your Guide to Reopening the Workplace"; https://www.salesforce.com/work/; Copyright 2020 Salesforce.com, Inc.; last accessed on Sep. 11, 2020.
"Pervidi Paperless Inspections_Distancing Alerts—Covid-19—Pervidi Contact Tracing App for Businesses"; https://www.pervidi.org/physical-distancing-alerts-2/?gclid=CjwKCAjw5lj2BRBdEiwA0Frc9cBiJIXfsfXKI_eCrYIUR9356HcRM2QQfSePeWBC2lgcqOAi2pSZzBoCuaQQAvD_BwE; Copyright Techs4Biz 2020; last accessed on Sep. 11, 2020.
Apple.com; "Privacy-Preserving Contact Tracing"; https://covid19.apple.com/contacttracing; Apr. 2020; Copyright 2020 Apple Inc.; last accessed on Sep. 11, 2020.
Kelton, Leo; BBC.com; "NHS rejects Apple-Google coronavirus app plan" https://www.bbc.com/news/technology-52441428; Apr. 27, 2020; Copyright 2020 BBC; last accessed on Sep. 11, 2020.
Chowdhury, Hasan, et al.; The Telegraph; "When will the NHS Covid-19 contact tracing app be ready—and how will it work?"; https://www.telegraph.co.uk/technology/2020/07/15/track-trace-app-uk-google-apple-when-download/; May 18, 2020; Copyright Telegraph Media Group Limited 2020; last accessed on Sep. 11, 2020.
Doffman, Zak; Forbes.com; "Forget Apple and Google: Contact-Tracing Apps Just Dealt Serious New Blow"; https://www.forbes.com/sites/zakdoffman/2020/05/12/forget-apple-and-google-contact-tracing-apps-just-dealt-serious-new-blow/#7341f7502172; May 12, 2020; last accessed on Sep. 11, 2020.

* cited by examiner

*Primary Examiner* — Ted M Wang
(74) *Attorney, Agent, or Firm* — Dickinson Wright PLLC; Mark E. Scott

(57) ABSTRACT

Reducing the spread of contagions. At least one example embodiment is a computer-implemented method including: creating, by a server system, an indication of suspended micro-droplets of spittle in an area of a building; receiving, by the server system, an indication that a mobile device is moving toward the area of the building; and sending, by the server system, an alert to the mobile device, the alert indicating that entry into the area of the building is not safe based on the indication of suspended micro-droplets of spittle.

17 Claims, 12 Drawing Sheets

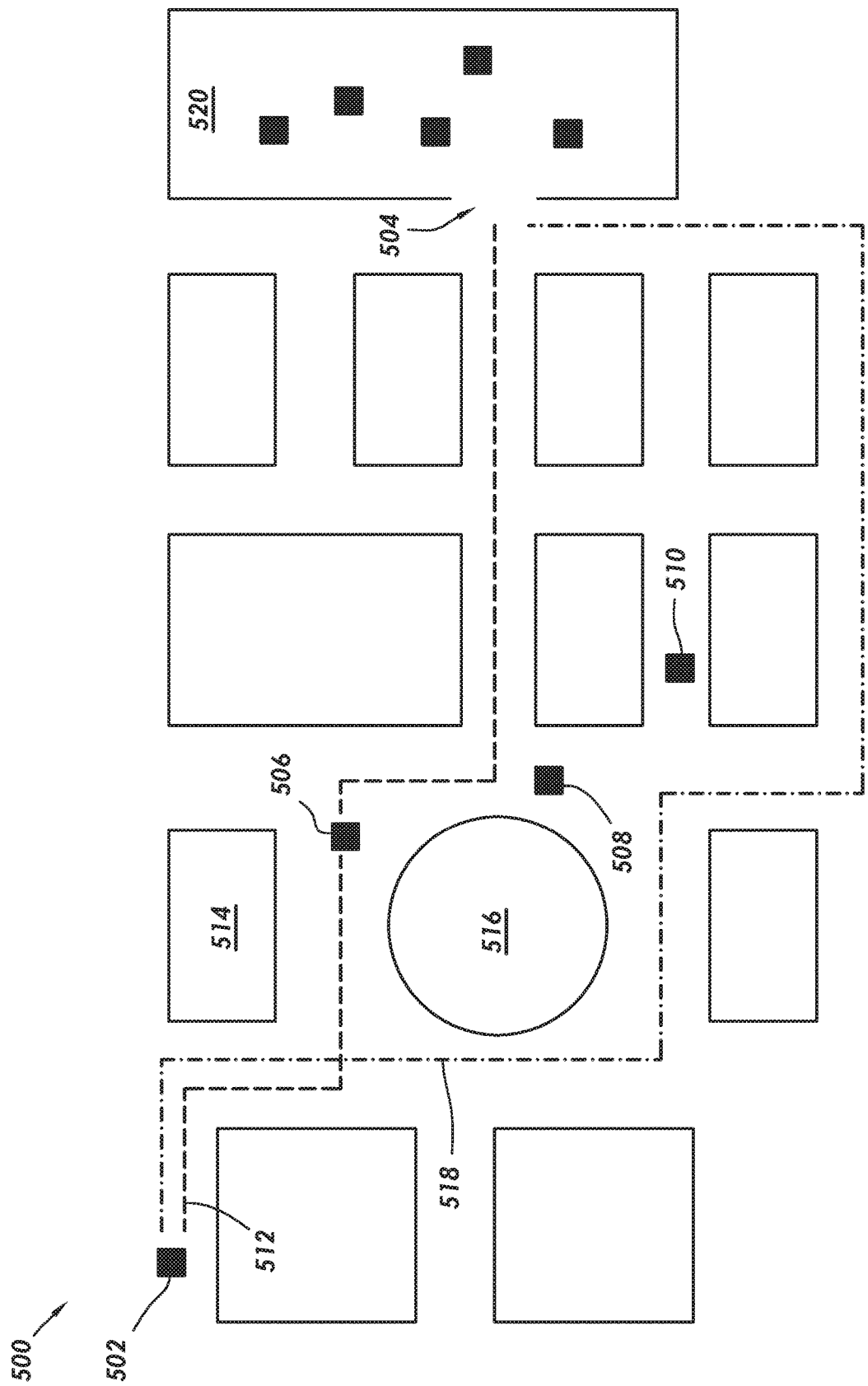

US 11,356,810 B1

METHODS AND SYSTEMS OF REDUCING THE SPREAD OF CONTAGIONS

CROSS-REFERENCE TO RELATED APPLICATIONS

Not Applicable.

BACKGROUND

With the emergence the severe acute respiratory syndrome 2 (SARS-CoV-2), there has been a renewed interest in the fields of contact tracing and related indoor and outdoor navigation to avoid exposure. Related-art navigation programs, particular indoor navigation programs, are not designed to handle the added complexity associated with social distancing to avoid exposure.

Thus, any method and/or system that improves navigation to avoid exposure, and makes contact tracing more robust, would provide a competitive advantage in the marketplace.

BRIEF DESCRIPTION OF THE DRAWINGS

For a detailed description of example embodiments, reference will now be made to the accompanying drawings in which:

FIG. 5 shows an overhead view of area for navigation in accordance with at least some embodiments;

DEFINITIONS

Figure 1:
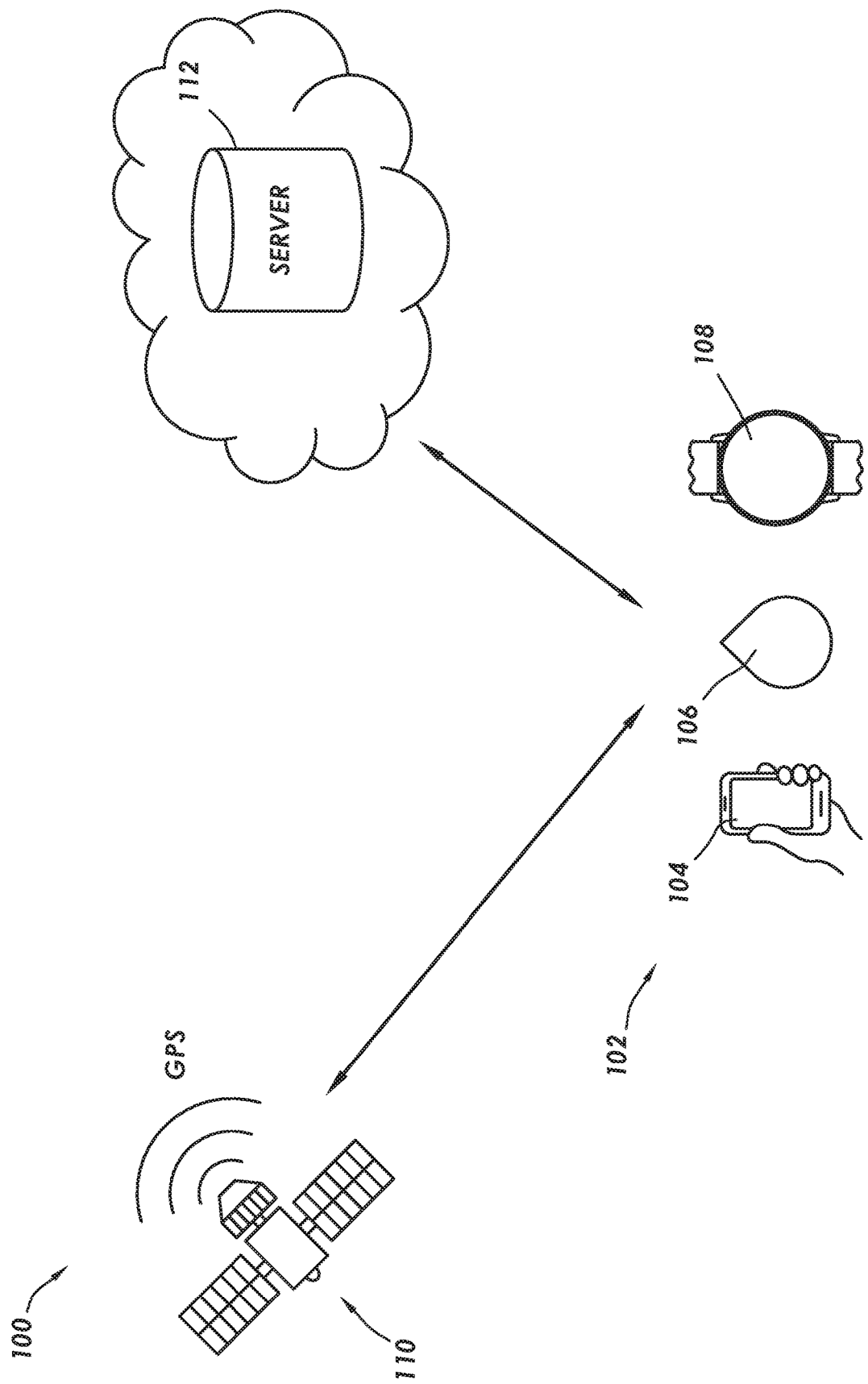
FIG. 1 shows an example system, in an outdoor context, in accordance with at least some embodiments.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

A growing body of knowledge regarding the severe acute respiratory syndrome 2 (SARS-CoV-2) indicates that micro-droplets of spittle created by a person breathing, talking, singing, and/or yelling may be a primary mechanism by which the SARS-CoV-2 is spread. A person may create tens of thousands of the micro-droplets of spittle during breathing, talking, singing, and/or yelling. The micro-droplets of spittle may be invisible to the naked eye in normal lighting conditions (e.g., 1 micro-meter ($\mu$m) to 500 $\mu$m), and because of the small size may be buoyed by molecules of air. That is, micro-droplets of spittle may hang or be suspended in the ambient air for an extended period of time (e.g., one to eight hours) depending on the location and the airflow through the area (e.g., indoor HVAC, or outdoor breeze). Thus, exposure may take place not only based on face-to-face contact with an infected person, but exposure may also take place by inhaling or otherwise coming into contact with the micro-droplets of spittle suspended in the air in an area previously occupied by the infected person. Related-art techniques of indoor and outdoor navigation, as well as contact tracing, cannot account for potential contagion exposure based on the historical presence of an infected person in an area, such as a partially enclosed outdoor space, an indoor space, an area within a building, a room within a building, or a workstation within a room within a building.

Various embodiments are directed to methods and systems of reducing the spread of contagions. Some example embodiments are directed to contact tracing taking into account historical presence. Other example embodiments are directed to enforcing social distancing in the context of indoor and outdoor navigation taking into account historical presence. The following is outline showing the organizational structure of the application:

I. Example System
  II. Contact Tracing
    A. Person-to-Person Contact
      (1) Peer-to-Peer Communication Contract Tracing
      (2) Location-Based Contact Tracing
    B. Historical Presence Contact Tracing
  III. Social-Distancing Based Navigation
    A. Navigation to Avoid Person-to-Person Contact
      (1) Avoidance Using Peer-to-Peer Communication
      (2) Avoidance Using Location-Based System
    B. Navigation to Avoid Historical Presence Contact
  IV. Location-Based Position Monitoring
    A. Assignment Monitoring
    B. Position Congestion Heat Mapping V. Improved Distance Calculations
VI. Geofencing
VII. Reliability Testing of Mobile Devices
VIII. Example Computer System The specification first turns to a high level overview of example systems.

I. Example System

FIG. 1 shows an example system. In particular, FIG. 1 shows a system 100 comprising three example mobile computing devices 102, hereafter singularly just mobile device 102 or as a group mobile devices 102. The example mobile devices 102 may take any suitable form, such as the mobile phone 104, a communication tag 106, or a smart watch 108. Other mobile devices 102 are possible, including laptop computer devices and tablet computer devices. Each of the example mobile devices 102 has the ability to determine its location by receiving signals from a global navigation satellite system (GNSS), such as the NAVSTAR global positioning system (GPS) operated by the United States government, or the BeiDou system operated by China. Regardless of the system used, a GNSS has a constellation of the satellites, illustrated by satellite 110, that send location signals to the mobile devices 102. From the timing of arrival of the location signals, each of the mobile devices 102 can determine its location, in some cases with an accuracy of 30 centimeters or better.

Each of the mobile devices 102 further comprises one or more wireless communication systems that enable communications between the mobile devices 102 and a remote computer system, illustratively shown FIG. 1 as a server computer system 112 (hereafter just server 112). The type of wireless communication depends on the situation and location of each of the mobile devices 102. For example, when outdoors, the mobile devices 102 may be communicatively coupled to the Internet, and thus server 112, by way of the data network of cellular communication system, such as a Global System for Mobile Communications (GSM) or Code-Division Multiple Access (CDMA) cellular network. In the example outdoor context, each of the mobile devices 102 may communicate over the cellular communication system.

In addition to or in place the communication by way of a cellular communication system, each of the mobile devices 102 may be communicatively coupled to the Internet by way of a short-range communication device and related protocol. For example, each of the mobile devices 102 may be communicatively coupled within a local area network, such as by way of any of the IEEE 802.11 family of communication standards. In yet still other cases, the short-range communication device and related protocol may be Bluetooth or near-field communication (NFC), ultra-wide band (UWB), or the like. Regardless, the example mobile devices 102 may be in communicative contact with the server 112 for purposes of social-distancing enhanced navigation and/or contact tracing. For example, as part of navigation and/or contract tracing (discussed in greater detail below), the mobile devices 102 may periodically report their location to the server 112.

The specification refers to actions taken by the server 112. It will be understood that the reference to actions taken by the server 112 refers to actions taken by one or more programs executed on or by the server 112. Moreover, the server 112 may itself be several distinct computer systems operated at the same or different physical locations, or one or more "cloud" computers whose identity and location may change based on computation load.

Figure 2:
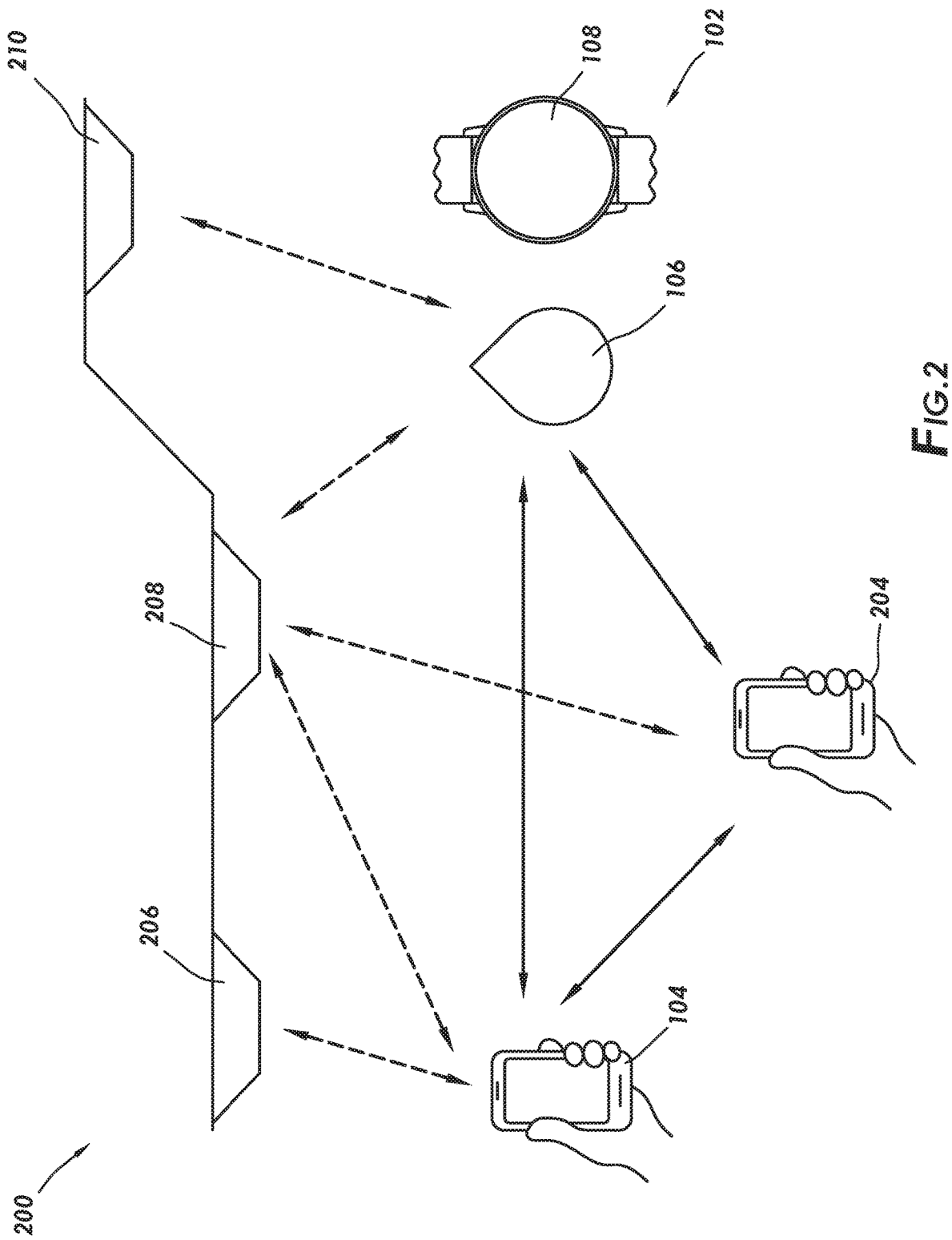
FIG. 2 shows an example system, in an outdoor context, in accordance with at least some embodiments.

FIG. 2 shows an example system at least partially in an indoor space. In particular, the example system 200 of FIG. 2 comprises the example mobile devices 102, including the mobile phone 104, the communication tag 106, and the smart watch 108. The example mobile devices 102 of FIG. 2 further include an additional mobile phone 202 to illustrate a point regarding peer-to-peer communication (discussed more below). The example system 200 further comprises a plurality of beacon devices, such as beacon devices 206, 208, and 210. The beacon devices may be placed at any suitable location, such as ceiling-mounted beacon devices, wall-mounted beacon devices, beacon devices mounted on structural pillars, and the like. The beacon devices 206, 208, and 210 may take any suitable form, such as Bluetooth Low Energy (BLE) devices, or UWB devices, available from many manufacturers. Using the example beacon devices 206, 208, and 210 (and possibly others), the mobile devices 102 can determination their location within an indoor space.

The location determination using the example beacon devices 206, 208, and 210 likewise may take many forms. In some cases, each beacon device 206, 208, and 210 periodically broadcasts a position signal that includes data that directly identifies the location of the respective beacon device within the indoor area. For each beacon device "heard" by any particular mobile device 102, the location of the mobile device may be determined in any suitable form, such as location matching the beacon (e.g., one beacon heard), as triangulation (e.g., three or more beacons heard), received signal strength indications (RSSI), and combinations of these techniques. In other cases, each example beacon devices 206, 208, and 210 may periodically broadcast a position signal, but that position signal may only identify the beacon itself, and not directly identify the location of the beacon within the indoor area. In such cases, the mobile devices 102 may download (e.g., from server 112) data that correlates the identity of the beacon to a location, and thus beacon location may be determined from the data. Again, for each beacon device "heard" by any particular one of the mobile devices 102, the location of the mobile device may be determined in any suitable form, such as location matching the beacon (e.g., one beacon heard), as triangulation (e.g., three or more beacons heard), RSSI calculations, and combinations of these techniques.

Still referring to FIG. 2, the example mobile devices 102 may also communicate directly with each other using one more short-range communication protocols, such as Bluetooth. For example, when in range the example mobile phone 104 may exchange information, such as identity information, with the mobile phone 204, the tag 106, and/or the smart watch 108. Similarly, when in range the example the mobile phone 204 may exchange information, such as identity information, with the mobile phone 104, the tag when in range the example 106, and/or the smart watch 108. When in range the example tag 106 may exchange information, such as identity information, with the mobile phone 104, the mobile phone 204, and/or the smart watch 108. When in range the example smart watch 108 may exchange information, such as identity information, with the mobile phone 104, the mobile phone 204, and/or the tag 106

Referring simultaneously to FIGS. 1 and 2. The system 100 of FIG. 1 and the system 200 of FIG. 2 are not mutually exclusive. In some situations the mobile devices 102 may be able to receive signals from both GPS satellites 110 and beacon devices 206, 208, and 210. For example, in a large atrium area or on patios of a hotel the mobile devices 102 may receive signals from GPS satellites high above the Earth and beacon devices installed for navigation within the building. Even some largely outdoor locations (e.g., football stadiums, baseball stadiums) may have beacons installed for navigation purposes, and the mobile devices 102 may receive signals from GPS satellites 110 and beacon devices 206, 208, and 210 within the structure. Further still, in some indoor locations (e.g., personal homes, doctor's offices) may not have beacons installed, and thus only peer-to-peer communications may be possible to determine relative locations. It follows that the separating the discussion into outdoor locations of FIG. 1 and indoor locations of FIG. 2 should not be read as a limitation as the applicability of any of the location determination systems and/or communicatively coupling scenarios of the mobile devices 102 to the server 112. Various aspects of both system 100 and system 200 may be present in any given situation.

II Contact Tracing

A. Person-to-Person Contact Tracing

The discussion now turns to various embodiments of contact tracing in the direct contact situation (e.g., two persons mutually present in an area), referred to herein as person-to-person contact tracing. The person-to-person contact tracing embodiments may be further conceptually divided into situations where location is determined by GPS satellites and/or beacon devices, and situations where the relative location is determined by peer-to-peer communication between mobile devices 102. The specification turns first to contract tracing in the peer-to-peer communication context.

(1) Peer-to-Peer Communication Contact Tracing

Still referring simultaneously to FIGS. 1 and 2. In accordance example embodiments each of the mobile devices 102 is communicatively coupled to the server 112 at relevant times during the contact tracing. Momentary loss of communication (e.g., moving through dead zones in the cell coverage, and/or moving with dead zones in Wi-Fi coverage) shall not obviate the communicative coupling between the mobile devices 102 and the server 112 at relevant times. In example systems, each mobile device 102 runs a contract tracing program or contract tracing application. When started, the contract tracing application establishes communication with and registers with the server 112. Responsive to the initial contact and registration, the server 112 may provide information, such as set of constants to be used in distance calculations using received signal strength indicator (RSSI) considerations, and other data and information described more below. A specific discussion of distance calculations, and the parameters used to improve the accuracy of the distance calculations for each specific device, are discussed in greater detail below in Section V (Improved Distance Calculations).

In the example system, upon a mobile device 102 making initial contact and registering with the server 112, the server may assign a unique identification number to the mobile device 102. The unique identification number may be used in ongoing communication between the mobile device 102 and the server 112. The unique identification number is also used in peer-to-peer communications with other mobile devices to ensure anonymity of communication between the devices. The unique identification number may be created in any suitable form, such as a hash function of an identifier of the mobile device. Each time a mobile device 102 comes within predetermined distance of another mobile device 102, one or both of the mobile devices 102 communicates the contact to the server 112. Consider, as an example, that mobile phone 104 registered with the server 112, and is periodically advertising its presence by broadcasting its unique identification number over a short-range communication protocol (e.g., Bluetooth). Similarly, consider that mobile phone 204 has registered with the server 112, and is periodically advertising its presence by broadcasting its unique identification number over the short-range communication protocol. The mobile phone 204 may receive the advertisement of mobile phone 104, and based on an RSSI calculation make a distance measurement between itself and the mobile phone 104. If the distance measured is equal to or less than a predetermined distance (e.g., two meters), the mobile phone 204 sends a notification to the server 112 indicating contact has been made, identifying itself by the unique identification number, and identifying mobile phone 104 by the unique identifying of mobile phone 104.

Mobile phone 204, receiving the advertisement from mobile phone 104, broadcasting its unique identification number over a short-range communication protocol. The mobile phone 104 may receive the advertisement of mobile phone 204, and based on an RSSI calculation make a distance measurement between itself and the mobile phone 204. If the distance measured is equal to or less than the predetermined distance (e.g., again two meters), the mobile phone 104 sends a notification to the server 112 indicating contact has been made, identifying itself by unique identification number, and identifying mobile phone 204 by the unique identifying of mobile phone 204.

If the owner of mobile phone 104 is later diagnosed with a contagion, such as SARS-CoV-2, the owner of mobile phone 104 may communicate the information to the server 112, the server 112 may search its database of stored contact information and determine all the mobile devices 102 that made contact with the owner of the mobile phone 104 (e.g., all mobile devices 102 that came within the predetermined distance of mobile phone 104). Thus, the example system may perform contact tracing based on peer-to-peer communication between mobile devices even in the absence of location determinations by those mobile devices.

(2) Location-Based Contact Tracing

Still referring simultaneously to FIGS. 1 and 2. In the location-based contract tracing embodiments, again each of the mobile devices 102 is communicatively coupled to the server 112 at relevant times during the contact tracing. As before, each mobile device 102 runs the contract tracing program or the contact tracing application. Whether previously started (e.g., in the peer-to-peer case) or newly started, the contact tracing application establishes communication with and registers with the server 112. Responsive to the initial contact and registration, the server 112 may provide information, such the unique identification and a set of constants to be used in distance calculations using RSSI considerations, unique identification number, beacon location information, and the like.

In accordance with the location-based contact tracing aspects, each time a mobile device 102 comes within predetermined distance of another mobile device 102, the server 112 records the contact. However, in the location-based contact tracing cases it is the server 112 that makes the distance measurement and records the contact. That is, the mobile devices 102 periodically communicate (e.g., every second, every two seconds, every five seconds) their respective locations to the server 112, and using the location information the server 112 makes distances calculations or distance measurements to determine whether the mobile devices 102 came sufficiently close to each other (e.g., within two meters) to be considered contact. Consider, as an example, that mobile device 102 has registered with the server 112, and the mobile device 102 is periodically sending its location to the server 112 using the assigned unique identification number. The location may be established by the mobile device 102 in any suitable form, such as by GPS position, using beacon devices 206, 208, 210, or combinations. Similarly, consider that the mobile phone 204 has registered with the server 112, and the mobile phone 204 is periodically sending its location to the server 112 using the assigned unique identification number. The location may be established by the mobile phone 204 in any suitable form, such as by GPS position, using beacon devices 206, 208, 210, or combinations. The server 112 receives the periodic broadcasts of position from all the mobile devices 102, and for all mobile devices under consideration the server 112 makes a distance determined between each mobile device. If any one or more of the distances determined is equal to or less than the predetermined distance (e.g., two meters), the server 112 records an indication that contact was made.

In the example case, if the owner of mobile phone 104 is later diagnosed with a contagion, such as SARS-CoV-2, the owner of mobile phone 104 may communicate the information to the server 112. The server 112 may search its database of recorded contact information and determine all the mobile devices 102 that made contact with the owner of the mobile phone 104 (e.g., all mobile devices 102 that came within the predetermined distance of mobile phone 104). Thus, in the example system the server 112 may perform contact tracing based on locations determination by the mobile devices.

In some example embodiments, the distance measurement is an absolute distance independent of intervening objects. In yet still other cases, however, the server 112 may take into account various structural and/or environmental factors when making a determination to record a contact between any two mobile devices.

Figure 3:
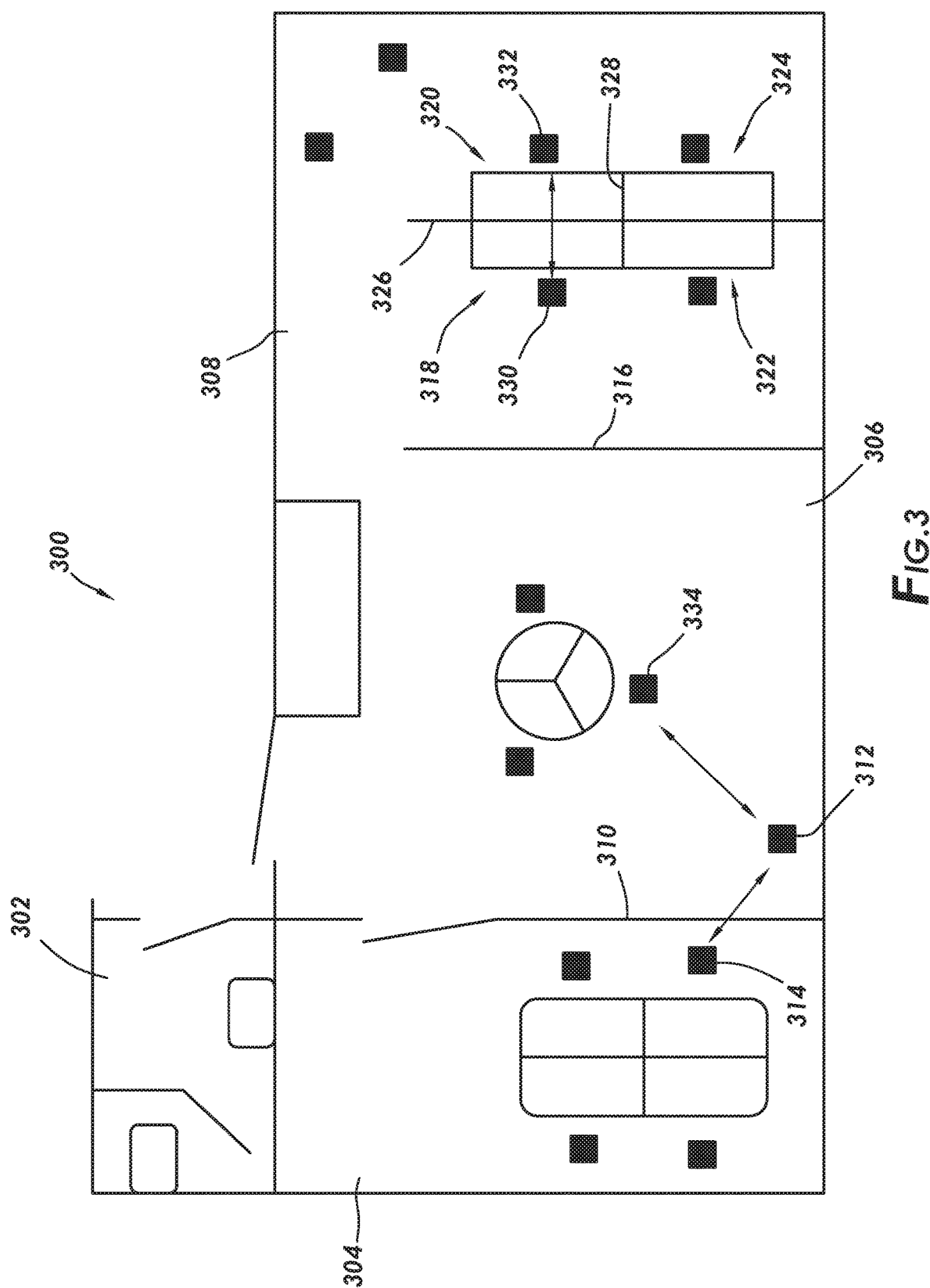
FIG. 3 shows an overhead view of an indoor area, in accordance with at least some embodiments.

FIG. 3 shows an overhead view of an indoor area in accordance with at least some embodiments. In particular, the example indoor area 300 defines four rooms or four zones 302, 304, 306, and 308. Though not specifically shown, consider that the indoor area 300 has disposed therein sufficient beacon devices (e.g., beacon devices 206, 208, and 210 of FIG. 2) such that mobile devices within the indoor area 300 are able to determine their location within the indoor area 300.

In the example embodiments, the server 112 may take into account various structural and/or environmental factors when making a determination as to whether to record a contact. In particular, in these example embodiments the server 112 knows or is provided information regarding the type of structures that make up or define the zones, air flow within the zones, and even within a zone may know the type of structures that define workstations (more on workstations below). Considering zones first, the server 112 may be provided information regarding the type and placement of walls within the indoor area 300 to define the zones. Considering the zone 304 as a representative, the server 112 may be provided information regarding the location, height, and type of materials that make up the walls that define the zone 304. For example, wall 310 between the zone 304 and the zone 306 may be designated as a sheetrock wall or a cinderblock wall. Moreover, the server 112 may be provided an indication of the height of the wall 310 (e.g., half-height wall, full-height wall). The information provided to the server may be extracted from architectural drawings, or may be determined based on a physical site visit to the indoor area 300.

The example server 112 (FIG. 1) may thus take into consideration the intervening structural information when making a determination as to whether to record a contact between the mobile devices. In the example embodiments, the server 112 (FIG. 1) receives, from each mobile device within the indoor area 300, an indication of location. The server 112 may make a distance determination between each mobile device. However, triggered by any two mobile devices being within the predetermined distance of each other, the example server 112 makes a further determination as to the presence of an intervening structure. The data regarding the intervening structure provides information regarding the extent that the intervening structure may block movement of suspended micro-droplets of spittle between the users of the mobile devices. If the intervening structure is considered sufficient to block movement of suspended micro-droplets of spittle, the server 112 may refrain from recording an indication that contact was made in spite of the mobile devices being within the predetermined distance.

Consider, as an example, a mobile phone 312 within zone 306. The mobile phone 312 may be any of the previously discussed mobile devices 102. In the example shown, the mobile phone 312 is close to wall 310, and another mobile phone 314 resides on the opposite side of the wall 310 in the zone 304. Further consider that mobile phone 314 is within the predetermined distance (e.g., two meters) from mobile phone 312. In accordance with example embodiments, the server 112 (FIG. 1) receives from each mobile phone 312 and 314 an indication of location within the indoor area 300. The server 112 may make a distance determination between the mobile phones 312 and 314. In this example case, and by assumption, the mobile phones 312 and 314 are within the predetermined distance. However, triggered by the mobile phones 312 and 314 being within the predetermined distance from each other, the example server 112 makes a further determination as to the presence of an intervening structures. In the case of FIG. 3, the wall 310 is an intervening structure. In this example case, the wall 310 is full height wall that is considered sufficient to block movement of suspended micro-droplets of spittle, and thus regardless of the distance and regardless of an amount of time the two example mobile phones 312 and 314 spend in close proximity, the server 112 refrains from recording an indication that contact was made.

Considering structures that make up zones within the indoor area 300 can also be extended to sub-zones or workstations within a zone. Still referring to FIG. 3, consider zone 308. The example zone 308 is defined by walls, such as wall 316 that separates zone 306 from zone 308. Within zone 308 resides four example sub-zones or four example workstations 318, 320, 322, and 324. Each of the workstations 318, 320, 322, and 324 may be, for example, a set of cubicles defined by air-impermeable panel structures with heights less than the height of the room. A set or group of panels may create the wall 326, and another set or group of panels may create the wall 328. The walls 326 and 328 thus define the four example workstations 318, 320, 322, and 324.

In the situation regarding zone 308, consider that a person with a mobile phone 330 resides at workstation 318, and that a person with a mobile phone 332 resides at workstation 320. Further consider that the mobile phone 330 is within the predetermined distance (e.g., within two meters) from the mobile phone 332. In accordance with example embodiments, the server 112 (FIG. 1) receives from each of the mobile phones 330 and 332 an indication of location within the indoor area 300. The server 112 may make a distance determination between the mobile phones 330 and 332. In this example case, and by assumption, the mobile phones 330 and 332 are within the predetermined distance. However, triggered by the mobile phones 330 and 332 being within the predetermined distance from each other, the example server 112 makes a further determination as to the presence of an intervening structure. In the case of FIG. 3 in zone 308, the wall 326 is an intervening structure. If the intervening structure is considered sufficient to block movement of suspended micro-droplets of spittle between the workstations 318 and 320, the server 112 may refrain from recording an indication that contact was made. Consider a case in which the wall 326 is relatively tall, for example, panels having a height of five feet or more. Assuming the workstations 318 and 320 are designed for work while sitting, a wall of 326 of five feet or more may be considered sufficient to block movement of suspended micro-droplets of spittle, and thus regardless of the distance and regardless of an amount of time the two example mobile phones 330 and 332 spend in close proximity, the server 112 refrains from recording an indication that contact was made. As an opposite example, consider a case in which the wall 326 is relatively short, for example, panels having a height of four feet less. Still assuming the workstations 318 and 320 are designed for work while sitting, a wall of 326 of four feet or less may be considered insufficient to block movement of suspended micro-droplets of spittle, and thus the server 112 may record an indication that contact was made as between users of the mobile phones 330 and 332.

In addition to, or in place of, the server 112 (FIG. 1) checking for intervening structures that may affect movement of suspended micro-droplets of spittle, the example server 112 may also take into consideration environmental factors that affect movement of suspended micro-droplets of spittle. That is, the example server 112 may take into consideration environmental factors in an area, a zone, or a workstation when making a determination whether to log a contact between the devices. In the example embodiments, the server 112 receives, from each mobile device within the indoor area 300, an indication of location. The server 112 may make a distance determination between each mobile device. Triggered by any two mobile devices being within the predetermined distance, the example server 112 may make a further determination as to the presence any mitigation environmental factors. If the mitigating environmental factor is considered sufficient to ensure the suspended micro-droplets of spittle cannot traverse the distance between the users of the mobile devices, the server 112 may refrain from recording an indication that contact was made in spite of the mobile devices being within the predetermined distance. If the mitigating environmental factor is considered insufficient to ensure suspended micro-droplets of spittle cannot traverse the distance between the users of the mobile devices, the server 112 may record an indication that contact was made. If the owner of one of the mobile devices is later diagnosed with a contagion, the owner of mobile device may communicate the information to the server 112, the server 112 may search its database of stored contact information to identify the contact.

Still referring to FIG. 3. Consider again, as an example, the mobile phone 312 within zone 306. Further consider that a mobile phone 334 is within the predetermined distance (e.g., two meters) from mobile phone 312. Further consider that the zone 306 has significant airflow, such as the ceiling-to-floor laminar air flow in a semiconductor fabrication facility. In accordance with example embodiments, the server 112 (FIG. 1) receives from each mobile phone 312 and 334 an indication of location within the indoor area 300. The server 112 may make a distance determination regarding a distance between the mobile phone 312 and 334. In this example case, and by assumption, the mobile phones 312 and 334 are within the predetermined distance. However, triggered by the mobile phones 312 and 334 being within the predetermined distance from each other, the example server 112 may makes a further determination as to an environmental factor, such as the presence or absence of the laminar air flow. If the example laminar air flow is present, the server 112 may refrain from recording an indication that contact was made. If the example laminar air flow is turned off or has insufficient velocity to ensure suspended micro-droplets of spittle cannot traverse the distance between the users of the mobile devices, the server 112 may record an indication that contact was made.

In yet still other cases, the environmental factor or factors may be taken into consideration in other ways. In particular, and as previously noted, in the location-based contact tracing embodiments each mobile device periodically sends its location information to the server 112 (FIG. 1). With the location information, the server 112 may identify a zone within which each mobile device resides. Each zone may be assigned its own specific predetermined distance that takes into account the environmental factor. For example, if the zone is a room in a semiconductor wafer fabrication facility having ceiling-to-floor laminar air flow, the predetermined distance may be selected to be smaller (e.g., 0.5 meter) to account for the environmental factor in the form of laminar air flow. As an opposite example, consider a storage room with no ventilation, and/or the ventilation system is off (e.g., a weekend). With little or no ventilation airflow, suspended micro-droplets of the spittle may easily travel greater distances than the example two meter predetermined distance, and thus in this example case the predetermine distance may be increased to effectively expand the predetermined distance that triggers recordation of a contact.

In other cases, the predetermined distance itself may remain unchanged for any area, zone, or workstation, but the predetermined distance may be modified by constant (termed herein an environmental constant) that takes into account the environmental factor. For example, in the example case of a semiconductor wafer fabrication facility having ceiling-to-floor laminar air flow, the predetermined distance may be multiplied by an environmental constant being less than one to make the net predetermine distance shorter for trigging a recordation of a contact. As an opposite example, consider the storage room with no ventilation. With little or no ventilation airflow, suspended micro-droplets of the spittle may easily travel greater distances than the example two meter predetermined distance, and thus in this example the environmental factor may be a value greater than one to make the net predetermine distance longer for trigging a recordation of a contact.

The various embodiments described with respect to FIG. 3 are in reference to an indoor area 300. However, the various embodiments of person-to-person location-based contact tracing are not limited to only indoor areas. The same techniques apply to outdoor areas, including taking into consideration intervening structures (whether natural or human made) as well as outdoor environmental factors (e.g., wind speed, wind direction, and temperature).

Moreover, the various embodiments described to this point have assumed that the server 112 (FIG. 1), when the circumstances dictate, records contact between devices in real time or near real time (e.g., within one minute of receiving location information from the mobile devices). However, in order to reduce processing time and resources, in yet still other cases the server 112 stores the location information, and any time-based environmental factors (e.g., HVAC on/off, laminar air flow handlers on/off), in a long term storage or database. The storage may take any suitable duration (e.g., seven to 21 days). If any user of any mobile device reports infection by a contagion, only after report is received does the server 112 invest the processor resources to determine the identity of the mobile device(s) that came within the predetermined distance of the infected person's mobile device, including taking into account environmental factors.

B. Historical Presence Contact Tracing

The discussion now turns to various embodiments of contact tracing based on historical presence (e.g., two persons in the same zone or workspace, but not at the same time), referred to herein as historical presence contact tracing. The historical presence contact tracing is based on reducing contagion infection caused by micro-droplets of spittle created by a person breathing, talking, singing, and/or yelling. Such micro-droplets of spittle may hang or be suspended in the ambient air for an extended period of time, in some cases from one to eight hours depending on the location and the airflow through the location. Thus, exposure to the contagion may take place not only based on face-to-face contact with an infected person, but exposure may also take place by inhaling or otherwise coming into contact (e.g., contact with the eyes) with the micro-droplets of spittle suspended in the air in an area previously occupied by the infected person.

In the historical presence contract tracing embodiments, the underlying functionality discussed with respect to the person-to-person contact tracing continues to be used. For example, each of the mobile devices is communicatively coupled to the server 112 at relevant times. Each mobile device 102 runs a contract tracing program or contract tracing application that establishes communication with and registers with the server 112. The server 112 provides information, such as a unique identification number, a set of constants to be used in distance calculations using RSSI considerations, data regarding location of beacon devices within the indoor space, and the like. Moreover, the contact tracing application and/or the server 112 may be designed and constructed to perform all the contact tracing embodiments discussed herein in relevant circumstances.

In accordance with the historical presence contact tracing embodiments, the server 112 (FIG. 1) may create an indication of presence of a first person in an area of a building (e.g., zone or workstation). The presence of the first person, and the first person's mobile device, within the area of the building may be fleeting (e.g., the mobile device merely passed through), or the presence of the first person's mobile device may be for extended periods of time (e.g., the first person worked in a zone or at a work station for an entire shift). The creation of the indication of presence may comprise receiving location information from the first person's mobile device indicating the mobile device is within the area of the building. Thus, for a fleeting presence, the server 112 may store a relatively small set of location information data. Oppositely, if the presence was for extended period of time (e.g., entire shift), the server 112 may store a relatively large set of location information data. After occupying the area of the building, the first person may depart the area, and thus location information provided by the first person's mobile device would no longer indicate presence in the area of the building.

The example server 112 (FIG. 1) may thereafter receive an indication that a mobile device of a second person entered the area of the building (e.g., the same zone, or the same workstation). The presence of the second person's mobile device within the area may also be fleeting, or the presence of the second person's mobile device may be for extended periods of time (e.g., the second person worked in the zone or at the work station of the first person for an entire shift).

If the first person is later diagnosed with a contagion, such as SARS-CoV-2, the first person may communicate the information to the server 112. That is, the server may receive an indication that the first person has a contagion. The server 112 may search its database of location information and determine that first person's mobile device and the second person's mobile device occupied the same area of the building, albeit at different times. Because of the overlap in occupied area of the building, the example server 112 may send an alert to the second person's mobile device indicating potential exposure to the contagion.

Figure 4A:
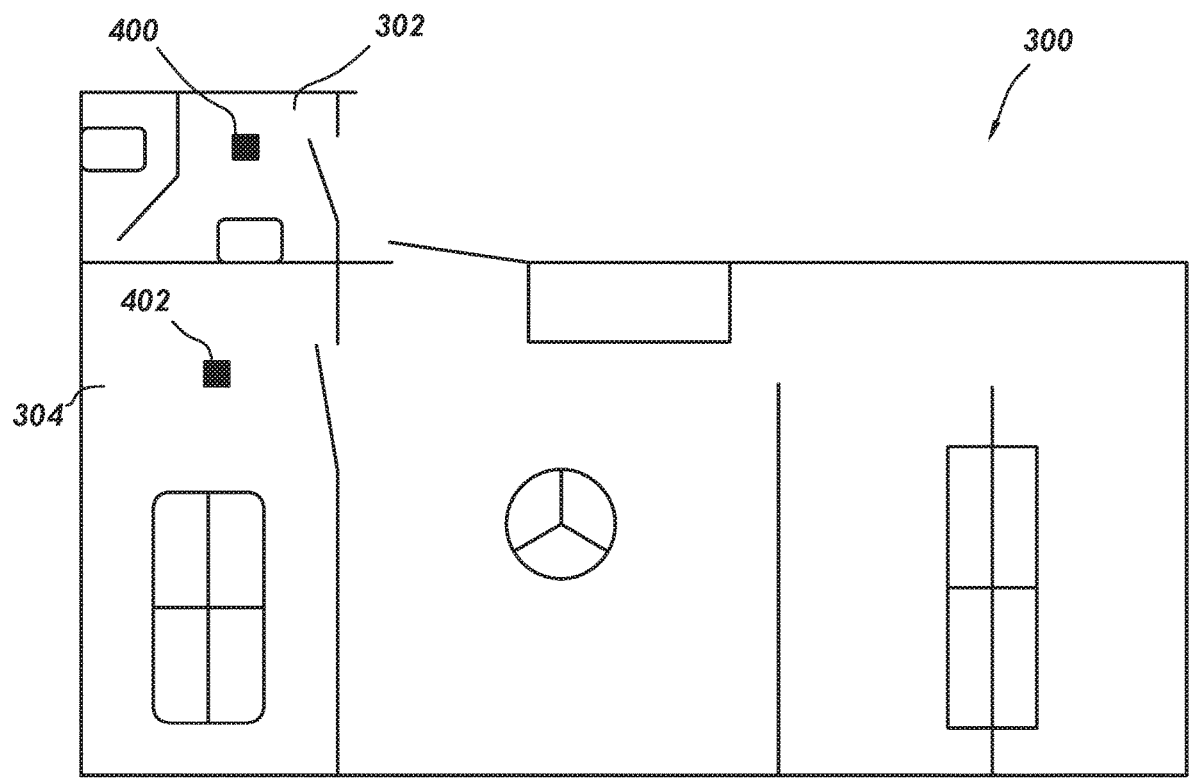
FIG. 4A shows an overhead view of an indoor area, in accordance with at least some embodiments.

FIG. 4A shows an overhead view of an example indoor area. Consider, as an example, a mobile phone 400 has registered with the server 112, and the mobile phone 400 is periodically sending its location information to the server 112 using the assigned unique identification number. The location may be established by the mobile phone 400 in any suitable form, such as by GPS position, using beacon devices 206, 208, and 210 (FIG. 2), or combinations. In the example situation of FIG. 4A, the mobile phone 400 reports location information indicating presence in the zone 302. Similarly, consider that a mobile phone 402 has registered with the server 112, and the mobile phone 402 is periodically sending its location information to the server 112 using the assigned unique identification number for the mobile phone 402. The location may be established by the mobile phone 402 in any suitable form, such as by GPS position, using beacon devices 206, 208, and 210, or combinations. In the example situation of FIG. 4A, the mobile phone 402 reports location information indicating presence in the zone 304. As shown in FIG. 4A, the mobile phone 400 and the mobile phone 402 are not in the same zone of the building, and are not close enough to trigger recordation of a person-to-person contact. In the example situation of FIG. 4A, the server stores the periodically sent location information generated by each of the mobile phones 400 and 402.

Figure 4B:
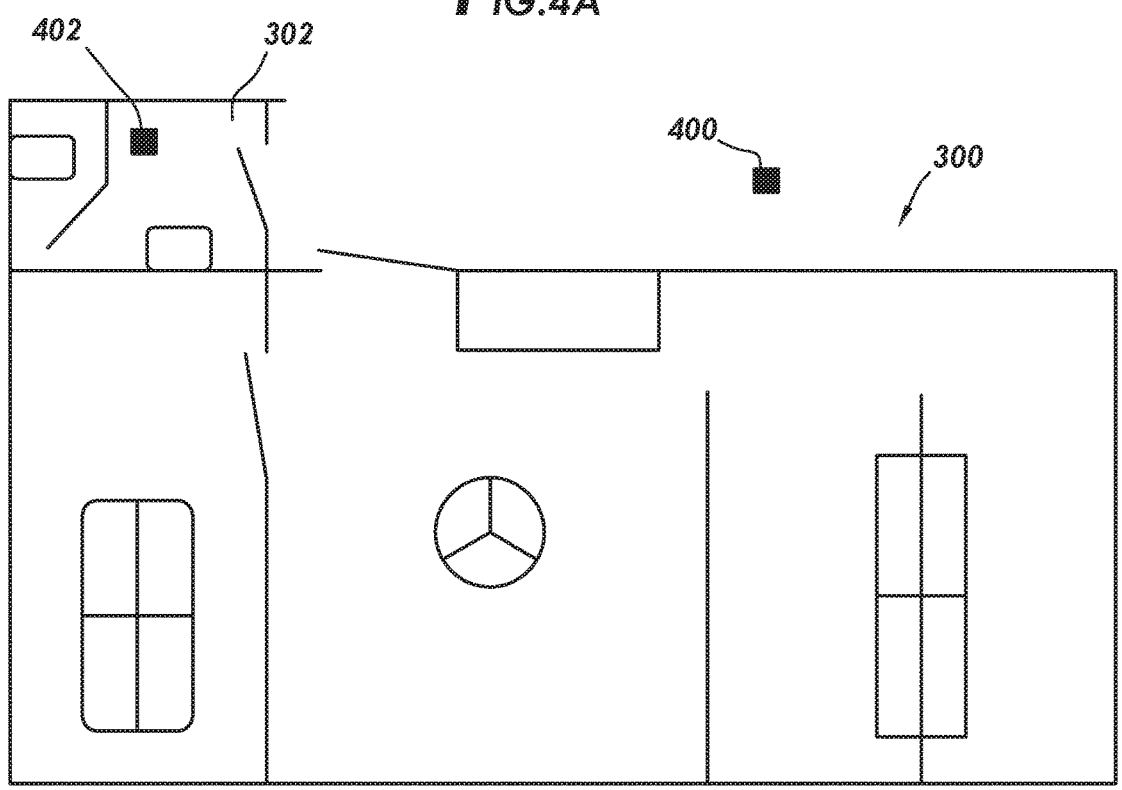
FIG. 4B shows an overhead view of an indoor area, in accordance with at least some embodiments.

FIG. 4B shows an overhead view of the example indoor area 300 at a point in time later than the FIG. 4A. In the example situation, the mobile phone 400 reports location information indicating a position outside the indoor area 300. Mobile phone 402 reports location information indicating a position in zone 302, the zone 302 previously occupied by mobile phone 400. As shown in FIG. 4B, the mobile phone 402 now resides in an area of building previously occupied by mobile phone 400. The server 112 may search its database of location information and determine that the mobile phone 400 earlier occupied the same area of the building. If the owner of the first mobile phone 400 is later diagnosed with a contagion, such as SARS-CoV-2, the first person may communicate the information to the server 112. The server 112 may search its database of location information and determine that mobile phone 400 and the mobile phone 402 occupied the same area of the building but at different times—non-concurrently co-location of two mobile devices. Because the overlap in occupied area of the building, the example server 112 may send an alert to the mobile phone 402 indicating potential exposure to the contagion. Thus, in the example system the server 112 may perform contact tracing based historical presence.

In some cases, making a determination of non-concurrently co-location of two mobile devices may be sufficient. However, in yet still further embodiments the determination of non-concurrent co-location within an area of the building may incorporate a time component. For example, the server 112 may receive an indication of presence of the first person within the area of the building, such as receiving location information from the first person's mobile device residing within the area. Later, the server 112 may receive an indication of departure of the first person's mobile device from the area (e.g., by receipt of location information indicating the first person's mobile device is in a different area). Based on a time of the initial indication of presence and the indication of departure, the server 112 may calculate of time of presence of the first person in the area of the building. From there, the example server 112 may assign, for the area of the building, a defined period after departure of the first person, the length of the defined period based on the time of presence of the first person. Applicants believe that, the longer the time of presence of the first person in an area, the greater the amount or volume of suspended micro-particles of spittle that will be present in the area. Moreover, the longer the period of time after departure of a person from the area of the building, the greater the likelihood that the suspended micro-particles of spittle have settled, and/or any contagion in such suspended micro-particles has been rendered harmless (e.g., breakdown based on temperature, or exposure to ultraviolet radiation). Thus, in example cases the longer the time of presence, the defined period will be longer, and oppositely the shorter the time of presence, the defined period will be shorter. If the second person's mobile device enters the area of the building within the defined period, the server may record a contact as between the first person's mobile device and the second person's mobile device. It follows that if later the first person reports infection with a contagion, the server 112 may thus send the alert to the second person's mobile device indicating potential exposure to the contagion.

Referring simultaneously to FIGS. 4A and 4B. Consider, as an example, the mobile phone 400 has registered with the server 112, and the mobile phone 400 is periodically sending its location to the server 112 using the assigned unique identification number. Further consider that the mobile phone 400 resides in zone 302 for an extended period of time (e.g., an entire shift), and thereafter departs zone 302 as shown in FIG. 4B. Upon the departure from the zone 302, the server 112 may calculate a time of presence of the mobile phone 400 in the zone 302. Based on the calculated time of presence, the server 112 may assign a defined period (e.g., one to eight hours). Further consider that the mobile phone 402 has registered with the server 112, and the mobile phone 402 is periodically sending its location to the server 112 using the assigned unique identification number. In the example situation of FIG. 4B, the mobile phone 400 reports location information indicating a position outside the indoor area 300, and the mobile phone 402 reports location information indicating a position in the zone 302, previously occupied by mobile phone 400. The server 112 may search its database of location information and determine not only that the mobile phone 400 earlier occupied the same zone 302, but that a defined period has been assigned by the server 112 regarding the zone 302. If the mobile phone 402 enters the example zone 302 within the defined period, the server 112 may record a contact as between the mobile phone 400 and the mobile phone 402. If the owner of the first mobile phone 400 is later diagnosed with a contagion, the first person may communicate the information to the server 112. The server 112 may search its database of location information and determine that mobile phone 400 and the mobile phone 402 were non-concurrently co-located (e.g., mobile phone 402 entered an area within a defined period). Because the overlap in occupied area of the building, the example server 112 may send an alert to the mobile phone 402 indicating potential exposure to the contagion.

In some cases, making a determination that a mobile device entered an area of a building within a defined period, selected based on prior presence of another mobile device, may be sufficient. However, in yet still further embodiments the determination of non-concurrent co-location within area of the building may incorporate a time component with respect to the second person as well. For example, the server 112 may receive the indication of presence of the second person within the area of the building, such as receiving location information from the second person's mobile device. Later, the server 112 may receive an indication of departure of the second person's mobile device from the area (e.g., by receipt of location information indicating the first person's mobile device is a different area). Based on a time of the initial indication of presence and the indication of departure, the server 112 may calculate of time of presence of the second person within the area of the building. From there, the example server 112 may make a determination as to the time of exposure of the second person to the suspended micro-particles of spittle created by the first person. Applicants believe that, the longer the time of exposure, the greater the amount or volume of suspended micro-particle of spittle that will be inhaled by or otherwise contacted by the second person. Thus, longer times of exposure (e.g., working at a workstation for an entire shift) represent a greater risk of catching the contagion, and oppositely shorter times of exposure (e.g., mere fleeting presence) represent a lesser risk of catching the contagion. If the second person's mobile device enters the area within the previously defined period, and the time of exposure is greater than a predetermined exposure time (e.g., two minutes, five minutes, an hour), the server 112 may record a contact as between the first person's mobile device and the second person's mobile device. It follows that if later the first person reports infection with a contagion, the server 112 may thus send the alert to the second person's mobile device indicating potential exposure to the contagion.

Still referring simultaneously to FIGS. 4A and 4B. Consider again that the mobile phone 400 has registered with the server 112, and the mobile phone 400 is periodically sending its location information to the server 112. Further consider that the mobile phone 400 resides in zone 302 for an extended period of time (e.g., an entire shift), and thereafter departs zone 302 as shown in FIG. 4B. Upon the departure from the zone 302, the server 112 may calculate a time of presence of the mobile phone 400 in the zone 302. Based on the calculated time of presence, the server 112 may assign a defined period (e.g., one to eight hours). Further consider that the mobile phone 402 has registered with the server 112, and the mobile phone 402 is periodically sending its location information to the server 112. In the example situation of FIG. 4B, the mobile phone 400 reports location information indicating a position outside the indoor area 300, and mobile phone 402 reports location information indicating a position in zone 302, previously occupied by mobile phone 400. Further consider that the mobile phone 402 resides in zone 302 for a period of time, and thereafter departs zone 302.

In the example situation, the mobile phone 402 resided in an area of building previously occupied by mobile phone 400. The server 112 may search its database of location information and determine not only that the mobile phone 400 earlier occupied the same zone 302, but that a defined period has been defined by the server 112 regarding the zone 302. Moreover, if the mobile phone 402 enters the example zone 302 within the defined period, the server 112 may calculate a time of presence of the mobile phone 402, and a time of exposure. In some cases, the time of presence of the mobile phone 402 and time of exposure will be the same (e.g., the mobile phone 402 entered the area just after departure of mobile phone 400 and departed after the expiration of the defined period). However, in other cases the time of presence may be different than the time of exposure. Consider, as an example, that the server 112 assigned a defined period of four hours based on the prior presence of the mobile phone 400. If the mobile phone 402 enters there area with only an hour remaining in the defined period, but the mobile phone 402 resides in the zone for six hours, the time of presence of the mobile phone 402 will be six hours, but the time of exposure will be only one hour. Nevertheless, if the time of exposure exceeds the predetermined exposure time, the server 112 may record a contact as between the mobile phone 400 and the mobile phone 402. If the owner of the first mobile phone 400 is later diagnosed with a contagion, the first person may communicate the information to the server 112. The server 112 may search its database of location information and determine that mobile phone 400 and the mobile phone 402 had a recorded contact, and the server 112 may send an alert to the mobile phone 402 indicating potential exposure to the contagion.

In addition to, or in place of, the various historical presence considerations discussed to this point, the example server 112 may also take into consideration environmental factors that affect movement of suspended micro-droplets of spittle in the historical presence contact tracing context. That is, the example server 112 may take into consideration environmental factors in an area, a zone, or a workstation, such as airflow, when making a determination whether to log a contact between the mobile devices based on historical presence. In example embodiments, the server 112 receives, from each mobile device within the indoor area 300 an indication of location. The server 112 may make a determination as to non-concurrent co-location between any two mobile devices. Triggered by any two mobile devices being non-concurrently co-located as discussed above, the example server 112 may make a further determination as to the presence any mitigating environmental factor. If the mitigating environmental factor is considered sufficient to ensure the suspended micro-droplets of spittle created by the first person have been cleared from the zone or workstation, the server 112 may refrain from recording an indication that contact was made in spite of the mobile devices being non-concurrently co-located. If the mitigating environmental factor is considered insufficient to ensure the suspended micro-droplets of spittle created by the first person have been cleared, the server 112 may record an indication that contact was made.

Still referring simultaneously FIGS. 4A and 4B. Consider again, as an example, the mobile phone 400 within zone 302. Further consider that the zone 302 has significant airflow, such as the ceiling-to-floor laminar air flow in a semiconductor fabrication facility. In accordance with example embodiments, the server 112 receives from the mobile phone 400 location information showing the mobile phone 400 is within the indoor area 300, and in particular zone 302. Further consider that the mobile phone 400 resides in zone 302 for an extended period of time (e.g., an entire shift), and thereafter departs zone 302 as shown in FIG. 4B. Upon the departure from the zone 302, the server 112 may calculate a time of presence of the mobile phone 400 in the zone 302. Based on the calculated time of presence, the server 112 may assign a defined period (e.g., one to eight hours). Further consider that the mobile phone 402 is periodically sending its location information to the server 112. In the example situation of FIG. 4B, the mobile phone 400 reports location information indicating a position outside the indoor area 300, and later the mobile phone 402 reports location information indicating a position in zone 302, previously occupied by mobile phone 400. Further consider that the mobile phone 402 resides in zone 302 for a period of time, and thereafter departs zone 302. Thus, the server 112 may make an initial determination that the mobile phone 400 and the mobile phone 402 were non-concurrently co-located (e.g., mobile phone 402 entered the zone during the defined period). However, triggered by the mobile phones 400 and 402 being non-concurrently co-located, the server 112 may make a further determination as to an environmental factor, such as the presence or absence of the laminar air flow. If the example laminar air flow is present, the server 112 may refrain from recording an indication that contact was made. If the example laminar air flow is turned off or has insufficient velocity to carry away the suspended micro-droplets of spittle, the server 112 may record an indication that contact was made.

In addition to, or in place of, the various mitigating environmental factors discussed to this point, the example server 112 may also take into consideration environmental factors that increase the amount or volume of suspended micro-droplets of spittle—aggravating environmental factors. Thus, the server 112 may take into consideration aggravating environmental factors in a zone or workstation that increase the chances of contagion spread when making a determination whether to record a contact between the mobile devices based on historical presence. Consider, as an example, ambient sound. If the first person worked silently at a workstation, the suspended micro-droplets of spittle created are limited to those created by respiration. Oppositely, if the first person talked continuously during the presence at the workstation (e.g., telemarketer) or sang boisterously during presence in the area of the building (e.g., member of choir), a greater amount or volume of suspended micro-droplets of spittle will be created. In the example embodiments, the server 112 receives an indication an ambient sound within the area of the building as potentially aggravating environmental factor. The receipt may be from sound noted by way of the microphone of the first person's mobile device, or from a microphone in a dedicated sound monitoring device (e.g., modified beacon device). When the server 112 makes a determination of non-concurrent co-location between any two mobile devices, the example server 112 may make a further determination as to the presence and/or magnitude of the aggravating environmental factor that increases the likelihood of exposure. The aggravating environmental factor may be considered in any suitable form, such as lengthening the defined period, or shortening the predetermined exposure time.

In yet still other cases, the environmental factor(s) may be taken into consideration in other ways. For example, each outdoor area, indoor area, zone, or workstation may be assigned its own specific formulae or equation for assigning the defined period, where the formulae or equation takes into account the aggravating and/or mitigating environmental factor(s). If the zone is a room in a semiconductor wafer fabrication facility having ceiling-to-floor laminar air flow, the defined period may be inversely related to airflow—the faster the laminar air flow, the shorter the defined period. As an opposite example, consider a storage room with no ventilation, and/or the ventilation system is off (e.g., a weekend). With little or no ventilation airflow, suspended micro-droplets of the spittle may hang in the air for a significant period of time, and thus in the storage room example the defined period may be increased to accommodate for suspended micro-droplets of spittle being hanging in the air for longer periods.

In other cases, the defined period calculated by the server 112 may remain unchanged for any area, zone, or workstation, but the defined period may be modified by an environmental constant that takes into account the environmental factor(s). For example, in the example case of a semiconductor wafer fabrication facility having ceiling-to-floor laminar air flow, the defined period may be multiplied by an environmental constant being less than one to make the net defined period shorter for trigging a recordation of a contact. As an opposite example, in the case of the storage room with no ventilation, the environmental factor may be a value greater than one to make the net defined period longer for trigging a recordation of a contact. As another example, the predetermined exposure time used by the server 112 may remain unchanged for any area, zone, or workstation, but the predetermined exposure time may be modified by an environmental constant that takes into account the environmental factor(s). For example, in the example case of a semiconductor wafer fabrication facility having ceiling-to-floor laminar air flow, the predetermined exposure time may be multiplied by an environmental constant being greater than one to make the net predetermined exposure time greater for trigging a recordation of a contact. As an opposite example, in the case of the storage room with no ventilation, the environmental factor may be a value less than one to make the net predetermined exposure time shorter for trigging a recordation of a contact.

The various embodiments described with respect to FIGS. 4A and 4B are in reference to an indoor area 300. However, implementations of historical presence location-based contact tracing are not limited to only indoor areas. The same techniques apply to outdoor areas, including taking into consideration defined areas (whether the defined areas are natural or human made) as well as outdoor environmental factors (e.g., wind speed, wind direction, and temperature). Other environmental factors that may be considered, including an intervening cleaning of the area (e.g., ultraviolet treatment of the air, and cleaning of the surfaces) and volume of the area (e.g. potential for exposure higher in a broom closet than a soccer stadium).

The location-based historical contact embodiments described to this point have assumed that the server 112, when the circumstances dictate, records a contact between devices in real time or near real time (e.g., within one minute of receiving location information from the mobile devices). However, in order to reduce processing time and resources, in yet still other cases the server 112 stores the location information, any time-based factors, and any environmental factors (e.g., HVAC on/off, laminar air flow handlers on/off), in a long-term storage or database. The storage may take any suitable duration (e.g., seven to 21 days). If any user of any mobile device reports infection by a contagion, only after the report is received does the server 112 invest the processor resources to determine the identity of the mobile device(s) that were non-concurrently co-located, including taking into time-based aspects and environmental factors.

III. Social-Distancing Based Navigation

The specification now turns to a related concept of social-distancing based navigation. That is, a mobile device providing indoor or outdoor navigation information while reducing the chances of two people coming within the predetermined distance to trigger a person-to-person contact, or reducing the changes of two people involved in non-concurrent co-location of an area. The social-distancing based navigation aspects may use the same underlying systems (e.g., GPS satellites 110, beacon devices, mobile devices 102, server 112, and related software), and in some cases further include a navigation component to reduce the chances of person-to-person contact and/or non-concurrent co-location. The specification first turns to navigation to avoid person-to-person contact.

A. Navigation to Avoid Person-to-Person Contact (1) Avoidance Using Peer-to-Peer Communication Referring again to FIGS. 1 and 2. In accordance example embodiments each of the mobile devices 102 is communicatively coupled to the server 112 at relevant times during navigation. Each mobile device 102 runs a navigation program or navigation application. The navigation application may be the same overall program as the contact tracing application, or a separate and distinct application. When started, the navigation application establishes communication with and registers with the server 112. Again, responsive to the initial contact and registration, the server 112 may provide information, such as set of constants to be used in distance calculations using RSSI considerations. The server 112 may assign a unique identification number to the mobile device 102, the unique identification number is used in further communication with the server 112, and the unique identification number used in peer-to-peer communications with other or secondary mobile devices, all to ensure anonymity of communication between the devices.

In accordance with the avoidance based on peer-to-peer communication, as the owner of a mobile device (hereafter the primary mobile device) traverses through an area where location cannot be determined, or cannot be accurately determined (e.g., an indoor area with no beacon devices), the navigation application of the primary device listens for periodic advertisements of presence of secondary mobile devices. If an advertisement from one or more secondary mobile devices is heard, several actions may take place. First, the primary mobile device likewise advertises its presence (to alert the secondary mobile device(s)). Secondly, the primary mobile device performs a distance calculation using RSSI techniques for each secondary mobile device heard, the RSSI calculation possibly including use of parameters downloaded from the server 112. Based on distance calculations, for each secondary mobile device outside a predetermined radius (hereafter the buffer zone), where the buffer zone is larger than the predetermined distance, the primary mobile device may take no action to alert the owner of the primary device. However, for each mobile device within the buffer zone, the primary mobile device may alert the owner (e.g., sound, display an alert on a display device) of a potential to come within the predetermined distance of the owner of the secondary mobile device. Based on the alert provided, the owner may change navigation route to avoid inadvertent contact. If the primary mobile device comes within the predetermined distance of a secondary mobile device, each of the primary and secondary devices may send an indication of contact to the server 112, using their respective unique identification numbers, as discussed above.

FIG. 5 shows an overhead view of area for navigation in accordance with at least some embodiments. For purposes of explanation, consider that FIG. 5 shows an indoor area 500 through which an owner of the mobile phone 502 desires to self-navigate. The various structures within the indoor area 500 may be, for example, booths within a convention center, the booths having sufficient height and opacity such that the owner of the mobile phone 502 cannot see over or around the various structures. Under these assumptions, the ability to perform visual avoidance is limited. Further consider that the owner of the mobile phone 502 desires to self-navigate from the initial location as shown in FIG. 5 to the destination location 504. Initially assume that the indoor area 500 does not contain beacon devices and that location signal from satellites are blocked.

The mobile phone 502 periodically advertises its presence by broadcasting its unique identification number over a short-range communication protocol (e.g., Bluetooth). Similarly, mobile phones 506, 508 and 510 periodically advertise their respective presence by broadcasting their respective unique identification number over the short-range communication protocol. The owner of the mobile phone 502 may initially desire to self-navigate along the route 512 (dashed line) to the destination location 504. The example owner of the mobile phone 502 may start initially along the route 512. While the mobile phone 502 may be aware of some or all the mobile phones 506, 508, and 510, based on distance calculations the secondary mobile devices are initially outside the buffer zone, and thus the mobile phone 502 may refrain from providing an alert. However, as the mobile phone 502 gets close to the mobile phone 506 (e.g., gets within the buffer zone), the mobile phone 502 provides an alert to the owner of mobile phone 502 indicating another mobile phone is within the buffer zone, and possibly indication a direction or range of directions toward the mobile phone 506. Thus, rather than making a left-hand turn between structure 514 and structure 516, the owner of the mobile phone 502 modifies travel direction to take route 518 (dash-dot-dash line) to avoid mobile phone 506. In the example, though the owner of the mobile phone 502 may initially plan to move back to the originally planned route 512 (by going around structure 516), the presence of yet another mobile phone 508 being within the buffer zone may result in yet another alert, forcing the owner of the mobile phone 502 to take another detour as shown by route 518. Further still, the presence of a third mobile phone 510 being within the buffer zone may force the owner of the mobile phone 502 to skirt the lower border of the indoor area 500 to reach the destination location 504. Thus, the owner of mobile phone 502 may self-navigate through the example indoor area with route changes to avoid contact with the other mobile phones with in indoor area.

In the peer-to-peer avoidance cases, the navigation at issue is self-navigation by the owner of the mobile phone 502 as, under the assumptions, the mobile phone 502 cannot determine its location. Nevertheless, the mobile phone 502 contributes to the self-navigation by providing alerts when other mobile devices are within the buffer zone. As a special case to the self-navigation, the peer-to-peer avoidance may also be used with respect to occupancy limitations for enclosed areas, such as meeting rooms. In particular, in accordance with the example embodiments the mobile devices, running the navigation application, may sense a plurality of secondary mobile devices in the vicinity of the primary mobile device. Thus, when the primary mobile device provides an alert to the user, the alert may identify not only that one or more secondary mobile devices are in the buffer zone, but the navigation program may also alert the user to the number of secondary devices in the buffer zone to help inform the user as whether to enter an enclosed area with an occupancy limit.

Still referring to FIG. 5, the example indoor area 500 further includes an example enclosed area in the form of a meeting room 520. Several mobile phones (not specifically numbered) reside within the example meeting room 520. Further consider that the example meeting room 520 has an occupancy limit of five persons. Using the peer-to-peer communication techniques, along with RSSI-based distance determinations, as the mobile phone 502 reaches the destination location 504 (i.e., the destination location 504 near the passageway into the meeting room 520), the mobile phone 502 may sense the plurality of the mobile phones within the meeting room 520. The mobile phone 502 may thus present an alert indicating not only that one or more mobile phones are within the buffer zone of the mobile phone 502, but the alert may also indicate the number of mobile phones within the buffer zone. Using the information, the user of the mobile phone 502 may make a determination as to whether to enter the meeting room based on the alert and the user's prior knowledge of the occupancy limit for the meeting room 520.

(2) Avoidance Using Location-Based System

The specification now turns to social-distancing based navigation with avoidance using the location-based system. Referring again briefly to FIGS. 1 and 2. Again, each of the mobile devices 102 is communicatively coupled to the server 112, and each mobile device 102 runs the navigation program or the navigation application. Whether previously started (e.g., in the peer-to-peer avoidance case) or newly started, the navigation application establishes communication with and registers with the server 112. Responsive to the initial contact and registration, the server 112 may provide information, such as the unique identification and a set of constants to be used in distance calculations using RSSI considerations. The mobile devices 102 periodically communicate (e.g., every second, every two seconds, and every five seconds) their respective locations to the server 112. Moreover, because the mobile devices 102 and/or the server 112 know the locations of the mobile devices, the mobile devices 102 may be provided data regarding layout of the location for purposes of navigation.

In accordance with the location-based avoidance navigation embodiments, the server 112 makes distance measurements regarding a distance between mobile devices 102, and provides routing information and/or alerts based on the distance measurements, location of other mobile devices within the area, and data regarding layout of the area. In particular, in the directed navigation context the server 112 takes into consideration location of other mobile devices in the area and data regarding layout of the area when plotting or planning a route. When the user is self-navigating or meandering (e.g., shopping), the location-based navigation embodiments may also provide alerts taking into consideration location of other mobile devices in the area and data regarding layout of the area. The routing information and alerts may be used to avoid entering the buffer zone of other mobile devices during the navigation.

More specifically, when a mobile device 102 requests routing information from a beginning location to a destination location, the server 112 generates a route that avoids any two mobile devices coming within the predetermined distance of each other (e.g., two meters). Even in absence of routing information provided by the server 112, such as when the owner of the primary mobile device is meandering within an area (e.g., shopping), the server 112 may generate alerts when the primary mobile device 102 is approaching (e.g., within the buffer zone) a secondary mobile device, and vice versa, to help the user of the primary mobile device avoid contact.

The location-based avoidance may also be used to with respect to occupancy limitations for enclosed areas, such as meeting rooms. In particular, the server 112 may sense that a plurality of mobile devices, and their respective owners, are in an enclosed area. Moreover, the server 112 may know in advance the occupancy limitation for the enclosed area. As the primary mobile device approaches the enclosed area, the server 112 may send an alert to the primary mobile device indicating that the enclosed area is at or above its occupancy limit. The primary mobile device, in turn, alerts the user that the enclosed area is unsafe to enter (e.g., sound, display an alert on a display device).

Referring again to FIG. 5. FIG. 5 is also representative of the location-based avoidance in the directed navigation case, and likewise shows an example location-based occupancy situation. Now consider that the indoor area 500 has beacon devices installed therein, and/or that location signals from satellites can be received in the indoor area 500. Thus, mobile devices in the indoor area 500 can determine their location. Again consider that the owner of the mobile phone 502 desires to navigate to the destination location 504. By way of the mobile phone 502, the server 112 is informed of the desired destination location 504. Responsive to receiving the request for routing to the destination location 504, the server 112 maps a route from the origin location (known based on the periodic location information sent to the server 112 by the mobile phone 502) to the destination location 504. Though the most direct route may be the route 512 (dashed line), the server 112 may map a route to avoid contact with the mobile phones 506, 508, and 510, and thus the location-based avoidance route may be the route 518 (dash-dot-dash line). To the extent any one or more of the mobile phones 506, 508, and/or 510 move during the journey of the mobile phone 502, the server 112 may provide updated route information, again to avoid any two mobile devices coming within the predetermined distance of each other (e.g., within two meters).

As before, the indoor area 500 further includes an example enclosed area in the form of the meeting room 520. In the location-based navigation cases, as the mobile phone 502 reaches the destination location 504 (i.e., the destination location 504 near the passageway into the meeting room 520), the server 112 may send to the mobile phone 502 an alert indicating that the meeting room 520 is at or above its occupancy limit. The mobile phone 502, in turn, alerts the user that the meeting room 520 is unsafe to enter, such as by sounding a tone or providing an indication on the display device of the mobile phone 502.

In some example cases, the distance measurement used by server 112 in the location-based navigation cases is an absolute distance (e.g., two-dimensional distance, three-dimensional distance) independent of intervening structures. In yet still other cases, however, the server 112 may take into account various structural and/or environmental factors when making a determination as to how close any two devices can be during navigation. In particular, and much like the location-based contact tracing embodiments discussed above, the server 112 knows or is provided information regarding the type of structures that make up or define an area. Moreover, the server 112 knows or may be provided information regarding the type of structures that define sub-areas (e.g., zones or workstations). The information provided to the server 112 may be extracted from architectural drawings, or may be determined based on a physical site visit to the indoor area.

When plotting a proposed route in the directed navigation case, the server 112 may make distance determinations regarding the distances between a plurality of locations defining the proposed route and the secondary mobile devices along the proposed route. If a distance determination reveals the proposed route will bring the primary mobile device within buffer zone (or closer) to a secondary mobile device, the example server 112 may then make a determination as the presence of an intervening structure between the proposed route and the secondary mobile device. The data regarding the intervening structure provides information regarding the extent that the intervening structure may be considered to block movement of suspended micro-droplets of spittle between. If the intervening structure is considered sufficient to block movement of suspended micro-droplets of spittle, the server 112 may disregard the mobile secondary mobile device and thus refrain from modifying the proposed route based on the presence of the secondary mobile device. Oppositely, if the intervening structure is considered insufficient to block movement of suspended micro-droplets of spittle, the server 112 may modify the proposed route based on the presence of the secondary mobile device.

When monitoring the location during self-navigation and/or meandering, the server 112 may make distance determinations regarding distance between the current location of the primary mobile device and the secondary mobile devices in the area. If a distance determination reveals the primary mobile device is within the buffer zone (or closer) to a secondary mobile device, the example server 112 may then make a determination as the presence of an intervening structures between primary mobile device and the secondary mobile device. If the intervening structure is considered sufficient to block movement of suspended micro-droplets of spittle, the server 112 may disregard the secondary mobile device and thus refrain providing an alert to the primary mobile device. Oppositely, if the intervening structure is considered insufficient to block movement of suspended micro-droplets of spittle, the server 112 may provide an alert to the primary mobile device.

In both the directed navigation case, and the meandering case, the server 112 may further determine a speed and direction of travel of one or both of the mobile devices, and take the speed and direction of travel into consideration. Taking the directed navigation case first, the example server 112 may calculate, based on an assumed or historical walking speed, the time of arrival of the primary mobile device at a series of locations along the proposed route. With respect the secondary mobile devices, the server 112 may not only make a distance determination regarding distance between the locations of the proposed route and the secondary mobile devices, but the example server 112 may also determine the speed and direction of travel of each of the secondary mobile devices. If, based on the speed and direction of travel of a secondary mobile device, the secondary mobile device will come within the buffer zone (or closer) at a location along the proposed route (without an intervening structure), the server 112 may modify the proposed route accordingly.

It is noted that, for long routes of travel, whether any secondary mobile device will intersect the proposed route may be indeterminate, particularly at the far ends of the route. Thus, in some cases the speed and direction of travel determinations regarding the secondary devices may be calculated only for devices within a predetermined region along the proposed route (e.g., for any secondary mobile device that could intersect the proposed route in the first 30 seconds of travel). Stated otherwise, if any particular secondary mobile device is beyond a predetermined separation from the primary device, then the secondary mobile device may be excluded from the speed and direction of travel calculations. When navigation actually begins, the server 112 may monitor secondary devices only within the predetermined region along the route when making determinations to modify the route based on the secondary mobile devices.

Taking the self-navigation or meander case next, the example server 112 may calculate the speed and direction of travel of the primary mobile device, and the speed and direction of travel of secondary mobile devices in the area. If, based on the speed and direction of travel of both the primary mobile device and the secondary mobile device, the two mobile devices will come within the buffer zone (or closer) of each other, the server 112 may send an alert to the primary mobile device, and the primary mobile device in turn provides the alert to the user (e.g., sound, display an alert on a display device). In order to reduce processor load, the speed and direction of travel determinations regarding the secondary devices may be calculated by the server 112 only for devices within a predetermined region around the primary mobile device. Stated otherwise, if any particular secondary mobile device is beyond a predetermined separation from the primary mobile device, then the secondary mobile device may be excluded from the speed and direction of travel calculations. The server 112 may monitor the secondary mobile devices only within the predetermined region when making determinations to send alerts to the primary mobile device regarding possible contact.

The discussion to this point makes a distinction between a primary mobile device and a secondary mobile device for purposes of explanation. However, the primary and secondary designation is only a point a view. The primary mobile device in all the examples above would be considered a secondary mobile device to other mobile devices in the area, each moving along a route and/or meandering within an area.

Figure 6:
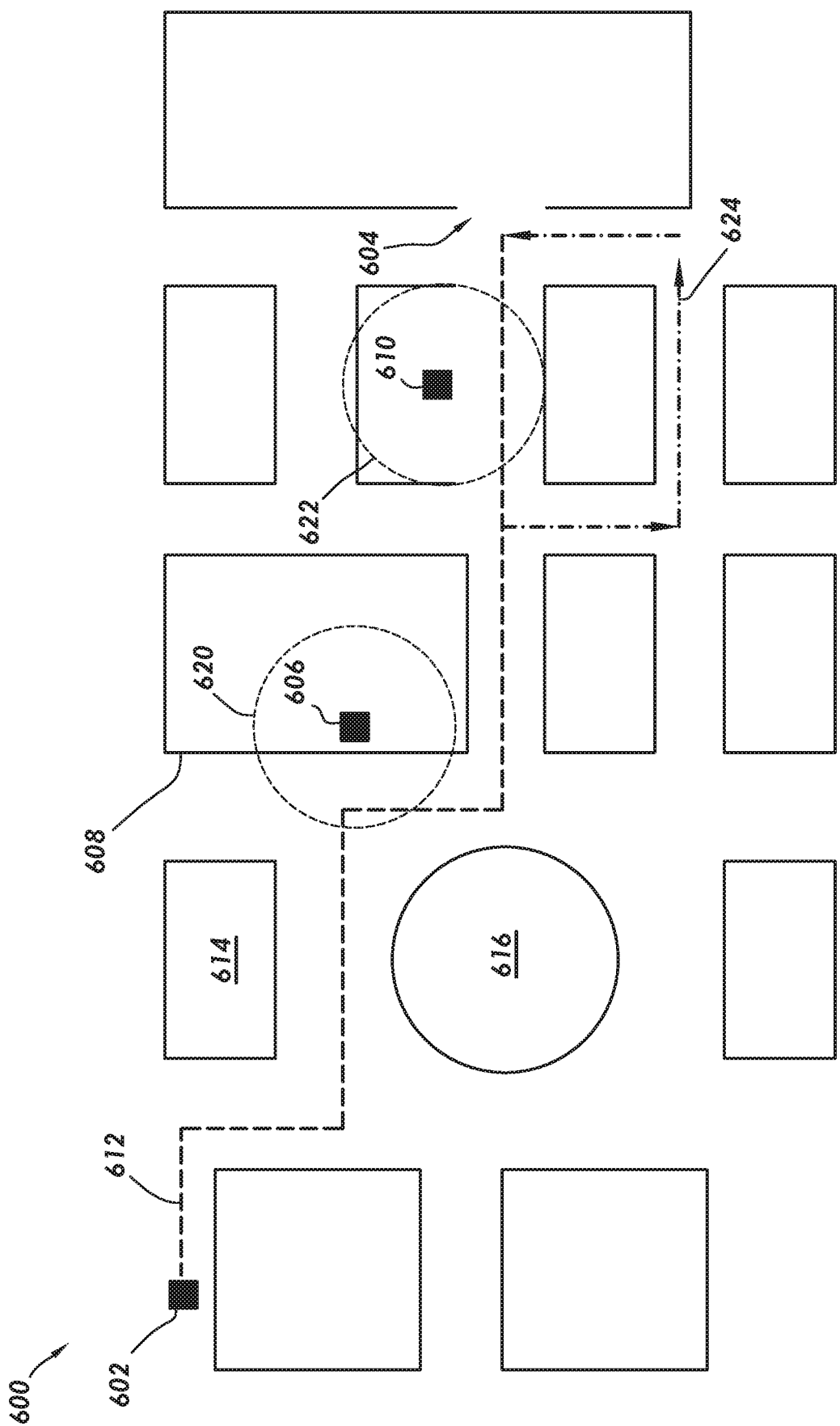
FIG. 6 shows an overhead view of area for navigation in accordance with at least some embodiments.

FIG. 6 shows an overhead view of area for navigation in accordance with at least some embodiments. Consider that FIG. 6 shows an indoor area 600 through which an owner of the mobile phone 602 desires to navigate. The various structures within the indoor area 600 may be, for example, booths within a convention center. Further consider that the owner of the mobile phone 602 desires to navigate from the initial location as shown in FIG. 6 to the destination location 604. Further assume that the indoor area 600 has beacon devices installed therein, and/or that location signals from satellites can be received in the indoor area 600. Thus, the mobile devices in the indoor area 600 can determine their location. By way of the mobile phone 602, the server 112 is informed of the desired destination location 604.

Considering the self-navigation or meandering case first. That is, the owner of the mobile phone 602 knows a route to the destination location 604, and thus does not contact the server 112 for routing information. Thus, the owner of the mobile phone 602 intends to take the route 612 (dashed line) to the destination location 604. In this example case, the owner of the mobile phone 602 starts along the route 512. As the mobile phone 602 traverses the route 612 between the structure 614 and the structure 616, the mobile phone 602 enters a buffer zone 620 associated with a mobile phone 606. That is, the server 112, monitoring the locations of both mobile phones 602 and 606 based on the periodic location information, determines that mobile phone 602 entered the buffer zone 620 of the mobile phone 606. It is equally accurate to say that the server 112, monitoring the locations of both the mobile phones 602 and 606, determines that mobile phone 606 entered a similarly sized and shaped buffer zone of mobile phone 602. Triggered by the breach of the buffer zone (regardless of how determined), the example server 112 may then make a determination as the presence of an intervening structure between mobile phone 602 and the mobile phone 606. In this example case, the wall 608 is considered sufficient to block movement of suspended micro-droplets of spittle (e.g., the wall 608 is an air-impervious wall greater than five feet tall). Since intervening wall 608 is considered sufficient to block movement of suspended micro-droplets of spittle, the server 112 may disregard the mobile phone 606 and thus refrain providing an alert to the mobile phone 602 as the mobile phone traverses the route 612.

As the example mobile phone 602 continues along the route 612, the mobile phone 602 enters a buffer zone 622 associated with a mobile phone 610 (or vice versa). That is, the server 112, monitoring the locations of both mobile phones 602 and 610, determines that mobile phone 602 entered the buffer zone 622 of the mobile phone 610. Triggered by the breach of the buffer zone (regardless of how determined), the example server 112 may then make a determination as the presence of an intervening structure between mobile phone 602 and the mobile phone 610. In this example case, there is no intervening structure between the mobile phone 602 and the mobile phone 610. Since there is no intervening structure considered sufficient to block movement of suspended micro-droplets of spittle, the server 112 may send an alert to the mobile phone 602. The mobile phone 602, in turn, provides the alert to the owner of the mobile phone 602 (e.g., sound, display an alert on a display device). Responsive to the alert, the owner of the mobile phone 602 may take an alternate route 624 (dash-dot-das line) to the destination location 604.

Now consider the directed navigation case in which the server 112 provides routing information to the mobile phone 602. That is, the owner of the mobile phone 602 requests from the server 112 a route to the destination location 604. The server 112, in turn, plots a proposed route, such as route 612. The server 112 may then make a distance determination regarding distance between a series of locations along the proposed route 612 and the secondary mobile devices along the proposed route, such as mobile phone 606 and mobile phone 610. Consider first mobile phone 606, in this example case the distance determination reveals the proposed route 612 will bring the mobile phone 602 within buffer zone 620 of mobile phone 606. Triggered by that determination, the example server 112 may then make a determination as the presence of an intervening structures between the proposed route and the mobile phone 606, and in this example the intervening structure is the wall 608. The data regarding the wall 608 shows the wall 608 is considered to block movement of suspended micro-droplets of spittle between the users of the mobile devices. Thus, the server 112 may disregard the mobile phone 606 and thus refrain from modifying the proposed route based on the presence of mobile phone 606.

Continuing along the proposed route 612, the server 112 continues making distance determinations between each location and the secondary mobile devices, such as mobile phone 610. Considering the mobile phone 610, in this example case the distance determinations reveals the proposed route 612 will bring the mobile phone 602 within buffer zone 622 of mobile phone 610. Triggered by that determination, the example server 112 may then make a determination as the presence of any intervening structures between the proposed route and the mobile phone 610, and in this example there is not intervening structure. Thus, the server 112 recalculates a modified route, such as route 624, to avoid the contact with the mobile phone 610.

In addition to, or in place of, the server 112 (FIG. 1) checking for intervening structures that may affect movement of suspended micro-droplets of spittle, the example server 112 may also take into consideration both aggravating and mitigating environmental factors that affect movement of suspended micro-droplets of spittle. The aggravating and mitigation environmental factors, as well example implementations, are discussed above and thus are not repeated again here so as not to unduly lengthen the specification.

The various embodiments described with respect to FIG. 6 are in reference to the indoor area 600. However, the various embodiments of location-based navigation are not limited to only indoor environments. The same techniques apply to outdoor environments, including taking into consideration intervening structures (whether natural or human made) as well as outdoor environmental factors (e.g., wind speed, wind direction, and temperature).

B. Navigation to Avoid Historical Presence Contact

The discussion now turns to various embodiments of navigation based on historical presence, referred to herein as historical presence navigation. In particular, historical presence navigation may involve providing alerts when the user is self-navigating or meandering, and providing routing information in the directed navigation context, that takes into consideration historical presence of persons. The alerts and/or routing information may be used to avoid locations of historical presence of persons to reduce contagion infection caused by micro-droplets of spittle created by the prior person breathing, talking, singing, and/or yelling at the historical location.

In the historical presence navigation embodiments, the underlying functionality discussed with respect to avoiding person-to-person contact in navigation (e.g., location-based navigation) may continue to be used. Moreover, the navigation application and/or the server 112 may be designed and constructed to perform all the navigation and contact tracing embodiments discussed herein, in relevant circumstances.

In accordance with the historical presence navigation embodiments, based on presence of person in an example area of a building, the server 112 may create an indication of suspended micro-droplets of spittle in the area of a building. The area of the building may be any area discussed above, such as a room in a building, a zone in the building, a workstation, or just an area in the building at which a person resided for a period of time.

The server 112 may thereafter receive an indication that a mobile device of a second person is moving toward the area of the building. The indication may take many forms. In the case of navigation from a beginning location to a destination location, the indication that the mobile device is moving may be the request for routing information, where an initial route includes moving through an area of historical presence of another person. In the case of a self-navigation or meandering (e.g., shopping), the indication that the mobile device is moving toward the area of the building may be data indicating that at the current speed and direction of travel the mobile device will intercept the area of historical presence.

The server 112 may therefore send an alert to the mobile device of the second person, the alert indicating that entry into the area of the building is not safe based on the indication of suspended micro-droplets of spittle. The alert may take many forms. In the case of directed navigation from a beginning location to a destination location, the alert may include providing, by the server 112 to the mobile device, a route that is not the most direct route or that is different than an initial route to the destination location. In some cases, the server 112 may provide data that shows the initial route, shows the safe route, and highlights the unsafe areas of historical presence of other persons. The mobile device, in turn, may provide the alert to the user, such as by showing the routes and unsafe areas on a map on the display of the mobile device. In the case of a self-navigation or meandering (e.g., shopping), the alert may indicate that, at the current speed and direction of travel, the mobile device will intercept the unsafe area of historical presence. Again in turn, the mobile device may provide the alert to the user in any suitable form (e.g., sound, display an alert on a display device).

Creating the indication of suspended micro-droplets of spittle may take many forms. In one example embodiment creating the indication of suspended micro-droplets may comprise receiving an indication of presence of a person within the area of the building (e.g., receiving by the server 112 periodic location information sent by a mobile device 102 to the server 112). In other cases, receiving an indication may include other, non-location information, such as receiving an indication of sound or voices within the area of the building. In the example case of receiving location information as an indication of presence, the server 112 may further receive an indication of departure of the person (e.g., receiving location information of the mobile device 102 shows the mobile device 102 is in a different area of the building). In some cases, the server 112 may calculate a length of time the first person's mobile device spent within the area of the building, for example, using time stamps associated with the indication of presence and indication of departure. The example server 112 may then generate the indication of suspended micro-droplets of spittle based on the indication of presence of the person, and in some cases the time of presence of the person within the area. For example, the server 112 may create a defined period based on any one or more of: the indication of presence; indication of departure, time of presence; and time of departure. That is, a non-zero defined period is an indication of suspended micro-droplets of spittle making the area unsafe.

Figure 7:
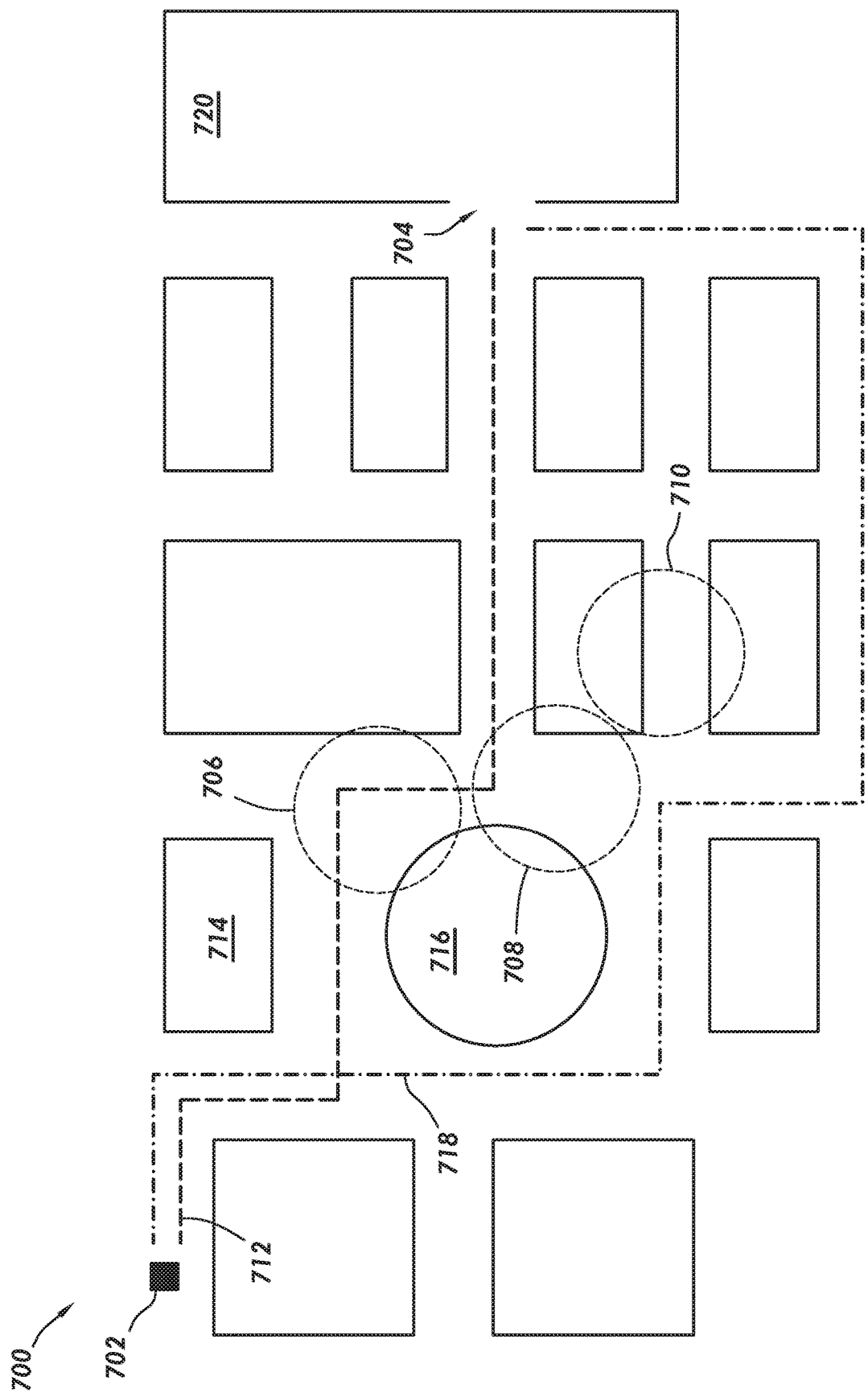
FIG. 7 shows an overhead view of area for navigation in accordance with at least some embodiments.

FIG. 7 shows an overhead view of area for navigation in accordance with at least some embodiments. For purposes of explanation, consider that FIG. 7 shows an indoor area 700 through which an owner of the mobile phone 702 desires to navigate. Further consider that the owner of the mobile phone 702 desires to navigate from the initial location as shown in FIG. 7 to the destination location 704. Assume that the indoor area 700 contains beacon devices and/or that location signal from satellites may be received. Thus, the example mobile phone 702 knows its location and provides periodic location information to the server 112 using its unique identification number.

In the example situation of FIG. 7, the server 112 has established three example areas of historical presence—area 706, area 708, and area 710. The example areas 706, 708, and 710 may take any form. As shown, the areas may be merely locations where a person or respective persons spent an extended period of time, and now the person(s) have departed the indoor area 700 or moved to other locations within the indoor area 700.

Consider that the owner of the mobile phone 702 desires to self-navigate from the current position as shown in FIG. 7 to the destination location 704. The mobile phone 702 periodically sends location information to the server 112. The owner of the mobile phone 702 may initially desire to take the route 712 (dashed line) to the destination location 704, and may start initially along the route 712. While the server 112 may be aware of the areas 706, 708, and 710 at the outset, given the self-navigation it may not yet be clear to the server 112 that the mobile phone 702, at the its current speed and direction of travel, will intercept an example areas 706, 708, and/or 710 (e.g., intercept within defined periods for the respective areas). Thus, the server 112 may initially refrain from providing an alert to the mobile phone 702. However, as the mobile phone 702 gets close to a defined area (e.g., area 706), the server 112 provides an alert to the mobile phone 702, and the mobile phone 702 in turn alerts the owner, in some cases providing: 1) an indication a direction of unsafe area (here, area 706); and 2) an indication of an alternate route to avoid the unsafe area (again, here area 706). Thus, in the example situation of FIG. 7, rather than making a left-hand turn between structure 714 and structure 716, the owner of the mobile phone 702 modifies the travel direction to take route 718 (dash-dot-dash line) to avoid unsafe area 706. Though the owner of the mobile phone 702 may initially plan to move back to the originally planned route 712 (by going around structure 716), the presence of yet another unsafe area 708 may result in yet another alert from the server 112 and mobile phone 702, forcing the owner of the mobile phone 702 to take another detour as shown by route 718. Further still, the presence of an unsafe area 710 may force the owner of the mobile phone 702 to skirt the lower border of the indoor area 700 to reach the destination location 704. Thus, the owner of mobile phone 702 may self-navigate through the example indoor area 700 with route changes suggested by the server 112 by way of alerts, all to avoid the example unsafe area 706, 708 and 710.

Still referring to FIG. 7, now consider a directed navigation case, in which the server 112 provides route information. By way of the mobile phone 702, the server 112 is informed of the desired destination location 704. Responsive to receiving the request for routing to the destination location 704, the server 112 maps a route from the origin location (known based on the periodic location information sent to the server 112 by the mobile phone 702) to the destination location 704. Though the most direct route may be the route 712 (dashed line), the server 112 may map a route to avoid moving through the unsafe areas of historical presence (e.g., areas 706, 708, and 710).

In some example cases, the server 112 provides the mobile phone 702 data that shows the most direct route 712, shows the safe route 718, and highlights the example unsafe areas of historical presence (e.g., areas 706, 708, and 710). The mobile phone 702, in turn, may provide the alert to the user, such as by showing the routes and unsafe areas on a map on the display of the mobile phone 702. The owner of the mobile phone 702 may thus traverse the safe route 718 to the destination location 704.

As before, the indoor area 700 further includes an example enclosed area in the form of the meeting room 720. The example meeting room 720 is shown in FIG. 7 to be unoccupied. However, for all the reasons previously discussed, the meeting room 720 may be considered an unsafe area based on historical presence of persons. For example, while the meeting rooms is shown unoccupied in FIG. 7, the meeting room 720 may have had a full occupancy load of persons for an extended period of time leading up the point in time shown in FIG. 7. Thus, in the historical presence avoidance embodiments, upon the mobile phone 702 entering a destination location targeting the meeting room 720, or having a course and speed that indicate an intent to enter the example meeting room 720, the server 112 may send to the mobile phone 702 an alert indicating that the meeting room 720 is unsafe to enter based on historical presence of others. The mobile phone 702, in turn, alerts the user that the meeting room 720 is unsafe to enter, such as by sounding a tone or providing an indication on the display device of the mobile phone 702.

As discussed in the Section II(B) above regarding historical presence contact tracing, the periods of time that the example areas 706, 708, and 710, and meeting room 720, are considered unsafe may incorporate a time component. For example, the server 112 may receive an indication of presence of person(s) within the area of the building, such as receiving location information from the mobile device(s) residing within the area. Later, the server 112 may receive an indication of departure of the mobile device(s) from the area. Based on a time of the initial indication of presence and the indication of departure, the server 112 may calculate of time of presence. From there, the example server 112 may assign, for the area, a defined period after departure with the length of the defined period based on the presence of the person(s), the time of presence of the person(s), and/or number of persons present. Applicants believe that, the longer the time of presence of person(s) in an area, the greater the amount or volume of suspended micro-particles of spittle that will be present in the area. Moreover, the longer the period of time after departure of the person(s) from the area, the greater the likelihood that the suspended micro-particles of spittle have settled, and/or any contagion in such suspended micro-particles has been rendered harmless (e.g., breakdown based on temperature, or exposure to ultraviolet radiation).

In addition to, or in place of, the various historical presence considerations discussed to this point, in yet still further embodiments the designation of an area of historical presence as unsafe by server 112 may also take into consideration environmental factors that affect movement of suspended micro-droplets of spittle in the historical presence context. That is, the example server 112 may take into consideration environmental factors in the example area or sub-area (e.g., zones or workstations), such as airflow through the within the area, when making a determination whether to designated an area as an unsafe area of historical presence. The same environmental factors discussed above, both mitigating and aggravating, are equally applicable in establishing the unsafe areas of historical presence by the server 112, and as such the environmental factors will not be repeated again here so as not to unduly lengthen the specification. Moreover, the various example methods of taking into consideration the environmental factors (e.g., directly establishing the defined periods, as environmental constant the modified the defined period) are equally applicable here in establishing the unsafe areas of historical presence by the server 112, and as such the methods of taking the environmental factors into consideration will not be repeated again here so as not to unduly lengthen the specification.

The various embodiments described with respect to FIG. 7 are in reference to the indoor area 700. However, implementations of navigation to avoid historical presence contact are not limited to only indoor areas. The same techniques apply to outdoor areas, including taking into consideration defined areas (whether the defined areas are natural or human made) as well as outdoor environmental factors (e.g., wind speed, wind direction, and temperature). As before, other environmental factors may be considered in establishing the unsafe areas of historical presence, including an intervening cleaning of the area (e.g., ultraviolet treatment of the air, and cleaning of the surfaces) and volume of the area (e.g. potential for exposure higher in a broom closet than a soccer stadium).

IV. Location-Based Position Monitoring

The specification now turns to monitoring location of persons in an area by way of mobile devices and using the location-based system. Referring again briefly to FIGS. 1 and 2. Again, each of the mobile devices 102 is communicatively coupled to the server 112, and each mobile device 102 runs a monitoring program or monitoring application. The monitoring application may be a standalone application, a functional component of the contact tracing applications, and/or a functional component of the navigation applications. The monitoring application establishes communication with and registers with the server 112. Responsive to the initial contact and registration, the server 112 may provide information, such as the unique identification and a set of constants to be used in distance calculations using RSSI considerations. The mobile devices 102 periodically communicate their respective locations to the server 112.

A. Assignment Monitoring

In accordance with example embodiments, the location-based system may be used to perform assignment monitoring of persons within an area. More particularly, the example monitoring application running on a mobile device, in conjunction with the server 112, may monitor location of a person as an indication that a person is fulfilling a work assignment. Consider that a first person has mobile device and has a work assignment in a defined area. The mobile device of the first person runs the monitoring application and periodically sends location information to the server 112. The server 112 receives in advance (e.g., by a mobile device of a supervisor) an indication of the location or area of the first person's work assignment, possibly along with shift assignment and/or an indication of work hours for the first person. The server 112 thus receives the periodic location information from the first person's mobile device during the work hours. The server 112, using the location information, may determine and/or calculate parameters associated with the first person's working habits. For example, the server 112 may determine parameters such as: time or times of entry of the first person into the work area; time or times of exit of the first person from the work area; movement within the work area during the work hours; and time spent within each sub-zone of the work area.

Figure 8:
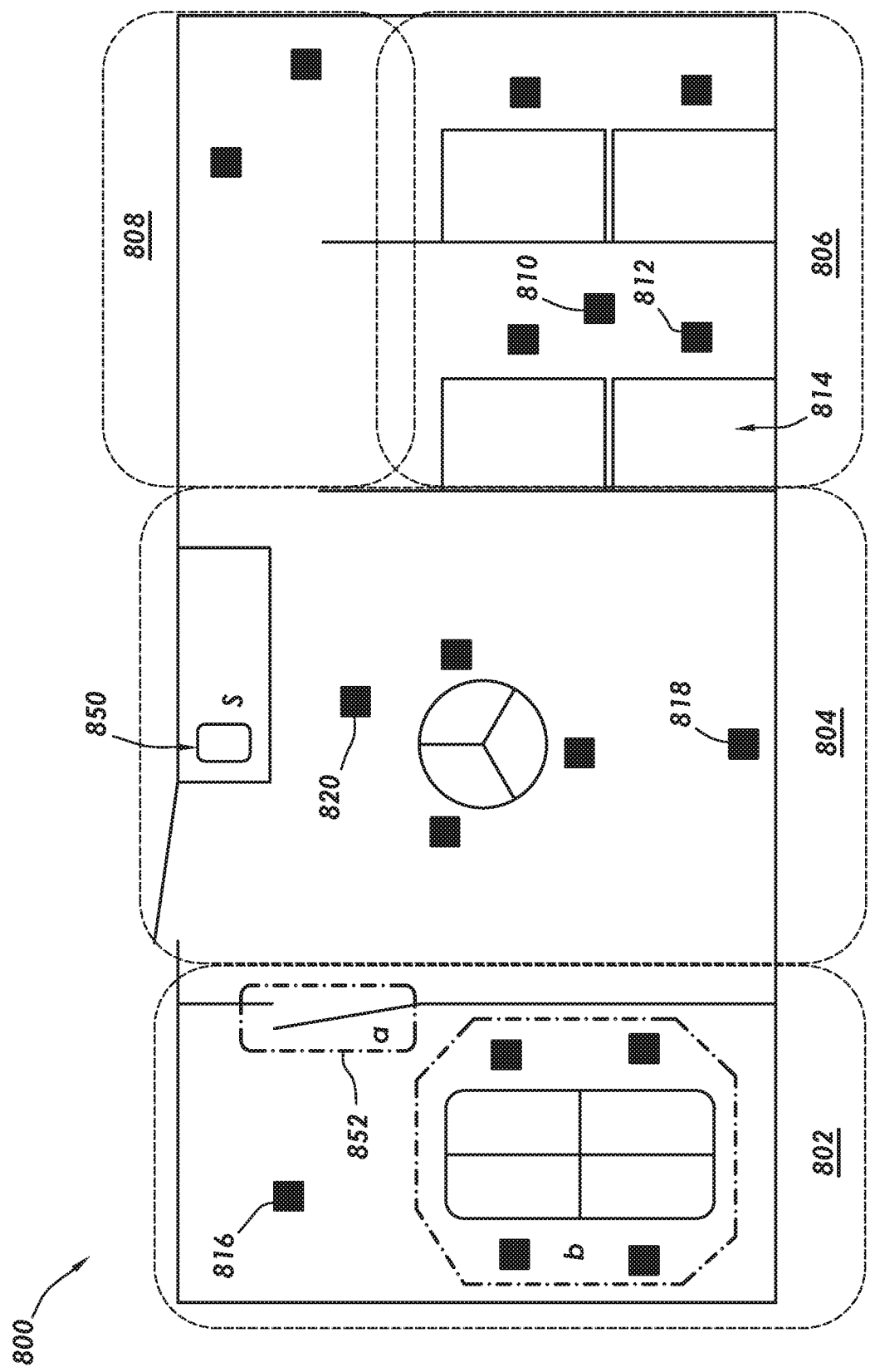
FIG. 8 shows an overhead view of an example work area in accordance with at least some embodiments.

FIG. 8 shows an overhead view of an example work area. Consider that the example work area is an indoor area 800 that contains beacon devices and/or that location signal from satellites may be received in the indoor area. Thus, mobile devices in the indoor area 800 know or can determine their location, and send periodic location information to the server 112. The example indoor area 800 may be conceptually divided into zones, such as zone 802, zone 804, zone 806, and zone 808. In some cases, the zones may be defined by walls or structures within the indoor area 800, such as zones 802 and 804. In other cases, the zones may be conceptual, dividing an otherwise open area, such as zones 806 and 808.

As an example of assignment monitoring, consider zone 806 and that mobile phone 810 is the mobile device of a supervisor. Further consider that the supervisor is required to be in the zone 806 of the indoor area 800 each morning between 07:00 and 07:30 (e.g., to greet the employees and provide work assignments). The supervisor's mobile phone 810 sends periodic location information to the server 112. The server 112, using the location information, may thus determine and/or calculate, on a daily basis, an indication of whether the supervisor occupied the example zone 806 at the during the designated time frame. Over the course of several work days, the server 112 may calculate a compliance score (e.g., 0 to 100%) as an indication of compliance with the work assignment of the supervisor. If the supervisor's mobile phone 810 is not in the defined zone 806 during the required hours, the server 112 may send an alert to another mobile device, such as the mobile device of the owner of the business.

Relatedly, consider that a mobile phone 812 in zone 806 is the mobile device of a worker. Further consider that the worker is required to be in the zone 806 of the indoor area 800 each day from 07:00 to 16:00 (e.g., to perform the tasks assigned by the supervisor). The worker's mobile phone 812 sends periodic location information to the server 112. The server 112, using the location information, may thus determine and/or calculate, on a daily basis, an indication of whether the worker occupied the example zone 806 over the course of the work day. Over the course of a work day or shift, or work days, the server 112 may calculate a compliance score (e.g., 0 to 100%) as an indication of compliance with the work assignment. Further still, consider that not only is the worker assigned to the zone 806, but that the worker is assigned to a particular workstation within the zone 806, such as workstation 814. Thus, the example server 112, using the periodic location information sent by the worker's mobile phone 812, may calculate a compliance score (e.g., 0 to 100%) as an indication of compliance with the worker's presence at the workstation 814 within the zone 806. If the worker's mobile phone 812 is outside the assigned zone 806 and workstation 814 for more than a predetermined absence, the server 112 may send an alert to the supervisor's mobile phone 810.

Still referring to FIG. 8, now consider the zone 802. In accordance with example embodiments the server 112 may also perform assignment monitoring in the form of acting as a time clock (e.g., logging arrival at work and departure from work). Consider, as an example, that mobile phone 816 is associated with a worker assigned to zone 802. The mobile phone 816, running the assignment monitoring application, periodically sends location information to the server 112. Thus, using the location information, the server 112 may make a determination that the mobile phone 816 entered the zone 802 at a particular time at the beginning of the work day. The server 112 may further monitor presence of the mobile phone 816 within the assigned zone 802 throughout the work day as discussed above. Again based on the periodic location information, the server 112 may make a determination that the mobile phone 816 departed the assigned work zone 802 at the end of the work day. Thus, using the periodic location information the server 112 may established a number of hours worked during any given work day.

In addition to, or in place of, monitoring for presence of a mobile device within a defined zone or workstation and/or acting as a time clock, the example system may also be used to control entry to areas within a building. Still referring to FIG. 8, consider that the doorway into zone 802 is itself assigned a zone 852. By monitoring when a mobile device enters the zone 852 from the right, with the intent to enter the zone 802 (e.g., intent inferred by speed and direction of travel, or pausing in the zone), the server 112 may make a determination as to whether the mobile device is authorized for entry. If authorized for entry, the server 112 may take steps to unlock or open the door, such as activating an electrically controlled lock or sending an alert to the mobile device that contains an entry code, or the like.

In addition to, or in place of, all the previous discussed location monitoring aspects, the example system may monitor and record movement within a zone. Consider zone 804, and a mobile phone 818 within the zone 804. Further consider that the mobile phone 818 belongs to sales associate assigned to the zone 804, and the example zone 804 is floor space in a retail establishment. In assisting customers to find various products, demonstrating products, answer questions about products, and the like, it is expected that a sales associate will travel throughout the zone over the course of a shift. Thus, example systems not only monitor the presence of mobile phone 818 within the zone 804 based on the location information sent to the server 112, but also determine a distance traveled within the zone. If, at a predetermined time during the shift (e.g., half-way point), the mobile phone 818 has traveled within the zone less than predetermined travel distance, the system may send an alert to the mobile phone 818 and/or the supervisor's mobile phone to alert regarding the performance shortfall.

Figure 9:
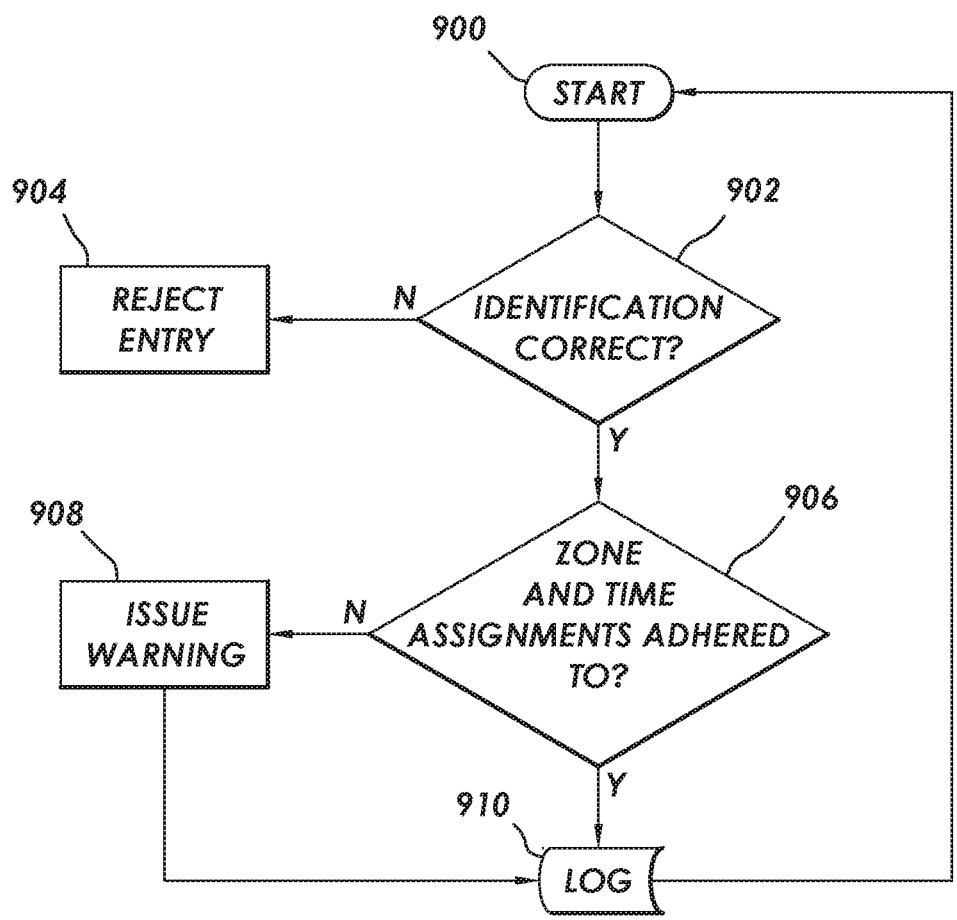
FIG. 9 shows a flow diagram of a monitoring method in accordance with at least some embodiments.

FIG. 9 shows a flow diagram of an example monitoring method. In particular, the method starts (block 900) and proceeds to making a determination as to whether the identification of a mobile device is correct for entry into an area (block 902). If the identification is not correct, entry into the area is rejected (block 904). If the identification is correct for entry into the area (again block 902), the example may proceed to enabling entry and making a determination as to whether the zone and time assignment were adhered to by the owner of the mobile device (block 906). If the zone and time assignment were not adhered to by the owner of the mobile device, the example method issues an alert or warning (block 908). Regardless of whether the zone and time assignments were adhered to, the example system logs the compliance or non-compliance (block 910), and the example method restarts for the next mobile device seeking entry (again block 900).

Returning to FIG. 8, as another assignment monitoring example consider that certain devices and/or locations need periodic attention and cleaning. For example, consider that within zone 804 there resides a point-of-sale (POS) device 850 at which customers perform self-checkout. Further consider that a member of janitorial staff carrying mobile phone 820 is assigned to clean the POS device 850 at regular intervals throughout the day. In the example system, and based on the periodic location information sent the server 112, the server 112 may make a determination as to how often throughout the day the mobile phone 820 comes within a predetermined range of the example POS device 850, and how long the mobile phone 820 stays within the predetermined range, all as an indication that the member of the janitorial staff cleaned the POS device 850 as assigned. In the event that a cleaning is missed, the server 112 may send an alert to the mobile phone 820 as reminder, and/or send an alert to the supervisor regarding the missed cleaning.

The various embodiments described with respect to FIG. 8 are in reference to the indoor area 800. However, implementations of monitoring work assignments are not limited to only indoor areas. The same techniques apply to outdoor areas, including taking into consideration defined areas (whether the defined areas are natural or human made).

B. Position Congestion and Heat Mapping

In accordance with example embodiments, the location-based system may also be used to perform congestion monitoring, and based on the congestion monitoring product "heat maps" showing locations of higher congestion. Here, "heat maps" do not refer to temperature, but instead refer to an indication of congestion within area or an indication of the number of mobile phones in an area over a given period of time. More particularly, the example monitoring applications running on respective mobile devices, in conjunction with the server 112, may monitor location of persons in an area as an indication of congestion within an area or a smaller region within the area. Knowing the location and/or extent of congestion within an area may lead to several downstream actions, such as controlling the frequency of cleaning, making suggestions regarding changes to flow of foot traffic, and/or making suggestions regarding additional partitions or screens to reduce the movement of suspended micro-droplets of spittle.

Figure 10:
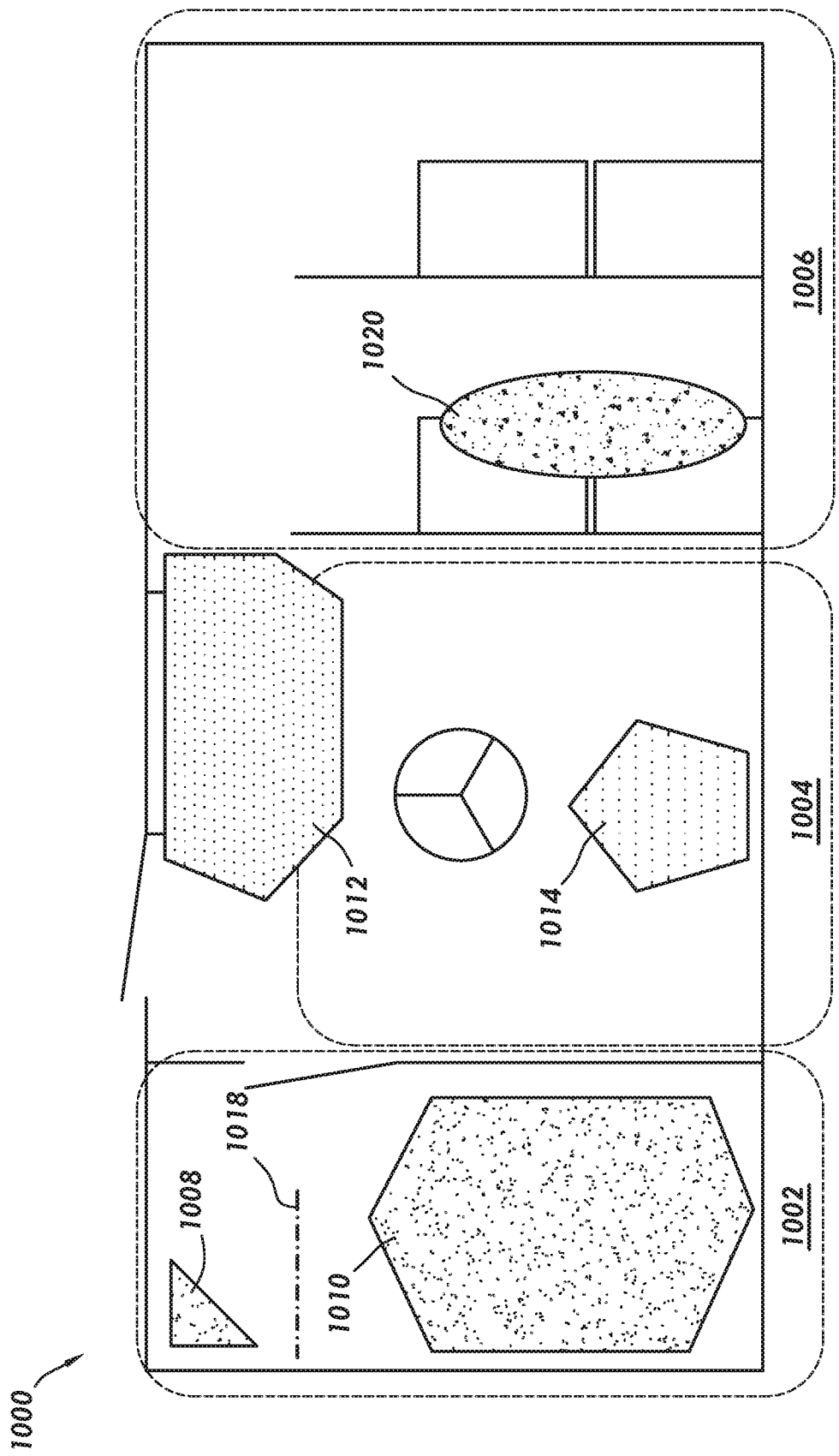
FIG. 10 shows an overhead view of an indoor area overlaid with a heat map in accordance with at least some embodiments.

FIG. 10 shows an overhead view of an indoor area overlaid with a heat map. In particular, FIG. 10 shows an indoor area 1000. The example indoor area 1000 is conceptually divided into zones 1002, 1004, and 1006. Each mobile device in the indoor area 1000 sends location information to the server 112. The server 112, in turns, may calculate or determine the number of mobile devices within a sub-zone or region over a given period time. The server 112 may establish or determine several regions of higher concentrations of mobile devices over the given period. For example, in zone 1002 the server 112 may determine the existence of two regions of concentration of the mobile devices, such as region 1008 and 1010. That is, each of the regions 1008 and 1010 may represent a region in which the number of mobile devices over a given period exceeds a predetermined threshold. Similarly, within zone 1004 the server 112 may determine regions of concentration of the mobile device, such as region 1012 and 1014. That is, each of the regions 1012 and 1014 may represent a region in which the number of mobile devices over a given period exceeds the predetermined threshold, and the thresholds need not be the same as between the zones or even between the regions within a zone.

Several points before proceeding. First, the regions determined may take any suitable shape to enclose or encompass areas in which concentrations of mobile devices over a given period exceed a predetermined threshold. Secondly, information can be extrapolated from the regions. Consider, as an example, the region 1012 which covers the location of the POS device (the POS device not visible in FIG. 10). Based on the heat map including a region that covers the POS device, the person or persons responsible for the zone 1004 may take action to reduce the spread of contagion caused by suspended micro-droplets of spittle. For example, a second POS device may be installed, or the area in and around the POS device may be cleaned with greater frequency.

Moreover, the heat maps may have a time component (in addition to the time component forming the regions). For example, if the situation of FIG. 10 occurs at shift change every day, then the server 112 may make suggestions to the reduce congestion, such as by reducing the number of the employees between specific times, staggering arrival times for the employees, re-arranging shift assignments, or making suggestions regarding changes to ventilation within the area to reduce the spread of contagion caused by suspended micro-droplets of spittle. As yet another example considering zone 1002, the server 112, analyzing the areas of congestion, may suggest additional structures to reduce travel distance of suspended micro-droplets of spittle, such as suggesting the placement of a wall, partition, or room divider 1018 (shown as a dash-dot-dash line).

The various embodiments described with respect to FIG. 10 are in reference to the indoor area 1000. However, implementations of congestion monitoring and creation of heat maps are not limited to only indoor areas. The same techniques apply to outdoor areas, including taking into consideration defined areas (whether the defined areas are natural or human made).

V. Improved Distance Calculations

Various embodiments discussed to point may make distance calculations based on RSSI considerations. For example, in peer-to-peer contact tracing, the distance between any two mobile devices may be calculated taking into account an RSSI component. Similarly, many of the location-based position determinations using beacon devices may use an RSSI component to establish the mobile device's distance from the beacon device(s). The specification thus turns to a discussion of an improved distance calculation that takes into account RSSI and various other parameters to make more accurate distance determinations between a mobile device and any other device.

In accordance with example embodiments, distance may be established or calculated by the mobile devices according the following equation:

$$D=10^{(P-A*RSSI)/10*N} \quad (1)$$

where D is the distance, P is a device-specific parameter, A is an area-specific parameter, RSSI is value indicative of remote signal strength provided by a transceiver of the mobile device, and N is a building-specific parameter. Each of the parameters P, A, and N will be discussed in turn.

In accordance with example embodiments, the parameter P is provided by the server 112. That is, the application running on the mobile device (e.g., contact monitoring application, navigation application, and/or location monitoring application) establishes communication with and registers with the server 112. Responsive to the initial contact and registration, the server 112 may provide information, such as the unique identification and the parameter P used in distance calculations using RSSI considerations. The example parameter P is a mobile-device specific parameter established in advance. More particularly still, the parameter P is determined for each brand and type of mobile device, and represents received signal strength "heard" by the mobile device when a test signal of predetermined power is broadcast at a predetermined spacing from the mobile device (e.g., 1 meter). For example, in the case of a mobile device in the form a mobile phone with an external antenna, the received signal strength for a test signal broadcast at the predetermined spacing may be higher than the received signal strength for a mobile phone with an internal antenna and/or a mobile phone that relies on the metallic casing as an antenna.

Regardless of the actual value of the parameter P, upon a mobile device establishing communication with the server 112, the server 112 determines the type of mobile device, performs a lookup operation (e.g., a table or database) to determine the parameter P, and sends the parameter P to the mobile device for use in distance calculations.

The example parameters A and N are area-specific and building-specific parameters, respectively. In peer-to-peer cases where the mobile device does not know its location, the mobile device may use default values for the parameters A and N. Alternatively, upon registration with the server 112 by a mobile device, the server 112 may send default values for the parameters A and N in the absence of the receiving location information from the mobile devices.

In situations where the mobile devices can receive location signals (e.g., from GPS satellites and/or beacon devices), the mobile devices periodically send location information to the server 112 as discussed above. Based on the location information, the server 112 in turns sends values for the parameters A and N based on the location. If an example mobile device is outdoors, the example server 112 may send default outdoor values for the parameters A and N.

If a mobile device is indoors, the server 112 may send values for the parameters A and N that are specific to the area and/or building defining the indoor location. In particular, the values for the parameters A and N may be determined in advance from review of architectural drawings, or the values for the parameters A and N may be determined based on a physical site visit to the indoor area during installation of the beacon devices, or thereafter.

Referring specifically to the area-specific parameter A, the value of the area-specific parameter A may range from zero to one, inclusive. The value selected may be a function of the mobile device type and/or physical aspects of the area. For example, if the building is constructed with or contains numerous walls and/or a significant number of vertical metallic structures defining the area, the value of the parameter A will be lower. Oppositely, if the building has large, wide-open regions with little or no intervening metallic structures, the value of the parameter A will be higher. Thus, for each area of a building, and for each device type, the server 112 may keep table or database of values of the area-specific parameter A to be provided to each mobile device.

Now referring specifically to the building-specific parameter N. The value of the building-specific parameter N may range from two to five, inclusive. The value selected may be a function of the mobile device type and/or physical aspects of the building. For example, N will be a higher number when no walls are present and will be higher when mobile device has strong RSSI capability. Oppositely, N will be lower when walls are present and will be lower when mobile device has weak RSSI capability. Thus, for each building, and for each device type, the server 112 may keep table or database of values of the building-specific parameter N to be provided to each mobile device.

The discussion to this point regarding the parameters A and N has assumed an area- and building-level set of parameters. However, in yet still further embodiments each zone or workstation within a building may have its own set of parameters A and N. Referring again to FIG. 10, for example, each zone 1002, 1004, 1006 may have its owns set of values for parameters A and N for each supported mobile device type. Moreover, even within a zone and for a consistent mobile device type, the values for the parameters A and N may be different. Consider, as an example, zone 1006. Zone 1006 may its owns set of values for parameters A and N for each supported mobile device type, and yet the workstations in shaded area 1020 may have more specific values for parameters A and N for each supported mobile device type that take into account physical aspects of the workstation.

VI. Geofencing

The discussion now turns to improvements in the selection and delivery of data from the server 112 to a mobile device regarding indoor navigation. In particular, in the location-based aspects of indoor navigation, the server 112 may provide to a mobile device data regarding the layout of the indoor area (e.g., for each floor of the building, the location of walls and doors). The size of data regarding the layout of an indoor area may be rather significant. Thus, any system or method that reduces the amount of data sent to the mobile device from the server, yet consistently provides relevant data for indoor areas visited by the mobile device, would improve the technical field of indoor navigation.

Referring again to FIGS. 1 and 2. In accordance with example embodiments a geofencing program or geofencing application runs on a mobile device 102. The geofencing application may be a standalone application, or the geofencing application may be a functional component of any of the previously discussed applications in this specification. In order to make available data regarding the layout of an indoor area, the geofencing application establishes geofences around a plurality of buildings in the vicinity of the location of the mobile device 102. A geofence is conceptual construct based on GPS location. In particular, a geofence can be considered a predefined boundary around a physical location. The boundary is not a physical boundary; rather, the boundary is programmatically tracked logical boundary around a physical location. Once a geofence is established, the mobile device 102 periodically determines whether the mobile device 102 has crossed the logical boundary. Crossing the logical boundary triggers an action. In the example cases here, a mobile device 102 crossing the logical boundary (i.e., crossing the geofence) triggers the geofencing application to request from the server 112 and download data regarding the layout of the indoor area associated with the geofence.

Many mobile devices commercially available at the time of drafting the current specification are pre-programmed (e.g., provided within the operating system of the mobile device) with the ability to establish geofences to trigger responsive action. For example, by providing a list of coordinates that define an enclosed area on the surface of the Earth, a geofence may be established. Once a geofence is crossed, the operating system generates an interrupt to trigger the responsive action, or otherwise the operating system triggers a predetermined routine to handle the responsive action. One technical shortcoming in some mobile devices that are commercial available at the time of drafting the current specification is a limitation regarding the number of geofences that can be maintained and monitored. For example, the IPhone brand product (available from Apple, Inc. of Cupertino, Calif.) has a technical limitation in that only 20 geofences may be established and monitored at any one time.

Example embodiments overcome the shortcomings of related-art devices by implementing predictive establishment of geofences for triggering downloading of data regarding the layout of the indoor area. In particular, in example case the geofencing application establishes a plurality of geofences around some buildings, but less than all buildings, in an area around or near the mobile device. The identity and location of the plurality of geofences is selected by the geofencing application based on several criteria. The first criteria may be buildings within a predetermined range from the current location of the mobile device. Another criteria may be buildings recently visited (e.g., within the last week, within the last month) by the mobile device. In yet still other cases, an artificial intelligence engine executed by the geofence application (or executed by the server 112), may be trained based on the historical data regarding locations visited by the mobile phone, and once at least partially trained the artificial intelligence engine may select some or all of the plurality of geofences established.

Figure 11:
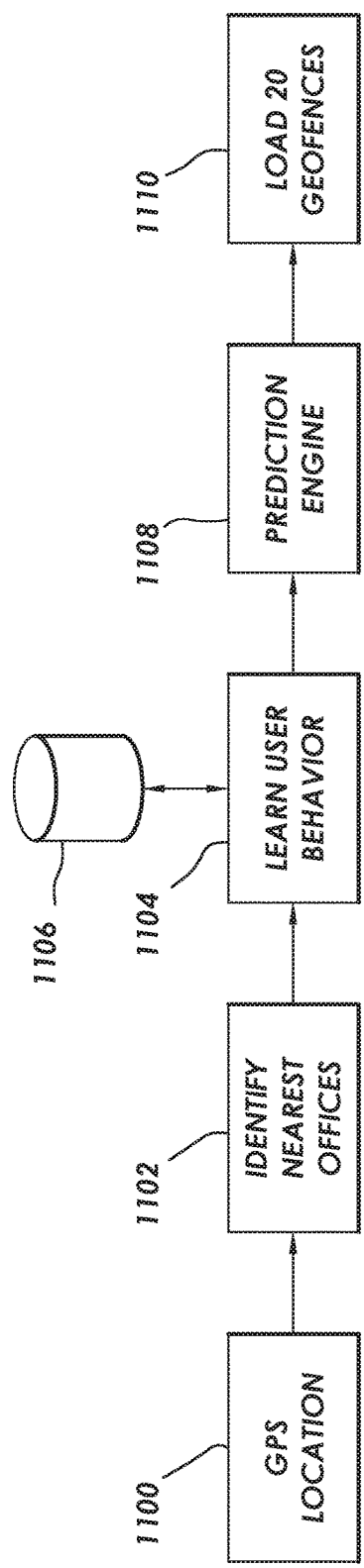
FIG. 11 shows a flow diagram of a method in accordance with at least some embodiments.

FIG. 11 shows a flow diagram of a method of selecting geofence locations. In particular, the example method starts with the mobile device determining its GPS location (block 1100). In example cases, the geofence application sends the location information to the server 112. The server 112, in turn, identifies a predetermined number of nearest offices or buildings (block 1102). Based on prior behavior of the owner of the mobile device (e.g., block 1104 and database 1106), the example method generates a data set being the conjunction of nearby offices or buildings and locations previously visited by the owner of the mobile device. The data set is provided to the example predication engine 1108. The predication engine, possibly including a trained artificial intelligence component, selects from the data set a predetermined number (less than all) of geofences from the data set. In the example case of the mobile device being an IPhone brand product, the predication engine 1108 may select 20 entries from the data set being greater than 20 entries. Regardless of the number selected, the data regarding the selected geofences are sent from the server 112 to the mobile device, and the mobile device, in turn, establishes the geofences (block 1110). When a geofence boundary is crossed by the mobile device, the mobile device downloads from the server 112 data regarding the layout of the indoor area associated with the geofence. With the data regarding the layout of the indoor area, the mobile device may thus perform indoor navigation and/or any of the previously discussed contract tracing methods and/or any of the previously discussed methods to reduce the spread of contagion.

Figure 12:
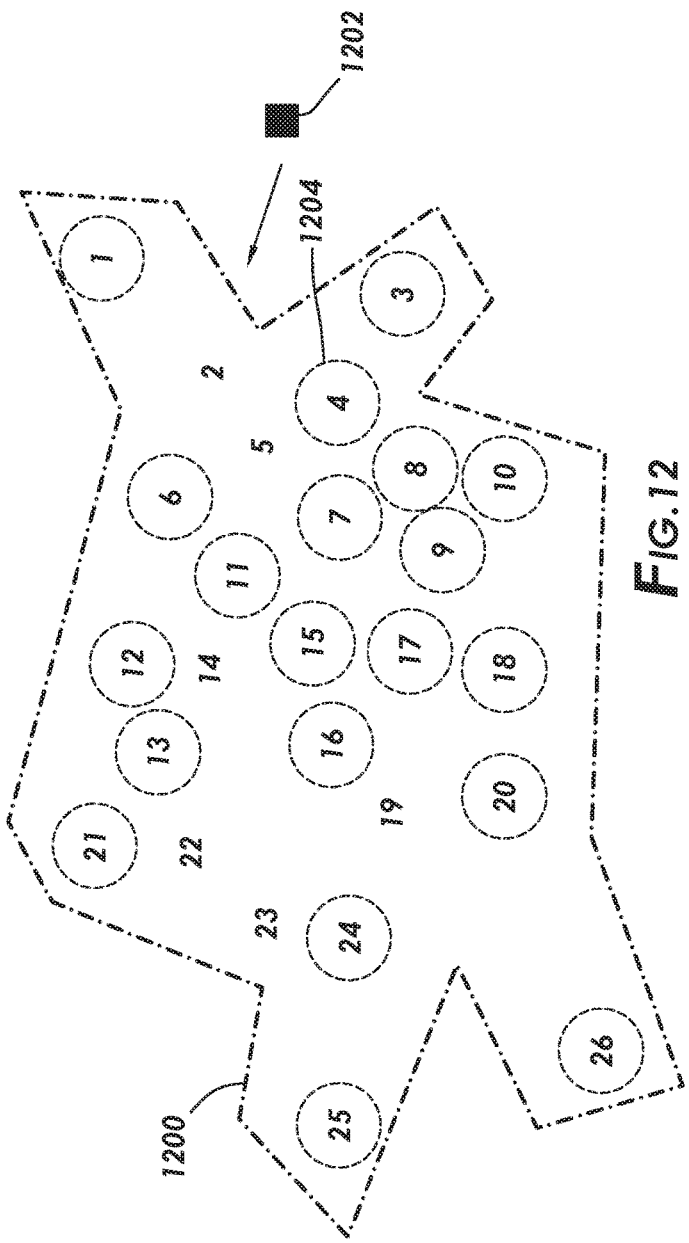
FIG. 12 shows an overhead view of a portion of a city or town, including a plurality of geofences, in accordance with example embodiments.

FIG. 12 shows an overhead view of a portion of a city or town, including a plurality of geofences. In particular, FIG. 12 shows an example political boundary 1200 (dash-dot-dash line). The political boundary 1200 may be, for example, the outer boundaries of the city limits of a city, or district within a city (e.g., a downtown district). Within the example political boundary 1200 resides a plurality of buildings, with the location of each building shown or designated by the location of a number. Thus, within the example political boundary there are 26 offices or buildings. Further consider that owner of the mobile phone 1202 lives, works, or plays regularly within the political boundary 1200, and thus the owner of the mobile phone 1202 has spent time in the past visiting various building within the political boundary 1200.

In accordance with example embodiments, as the mobile phone 1202 approaches the political boundary 1200, the mobile phone 1202 sends location information to the server 112. The server 112, in turn and in this example, identifies twenty buildings within the political boundary around which to established geofences (the geofences illustrated by dashed-line circles). The selection of the 20 buildings may be based, in part, on the identity of the buildings in the political boundary 1200 (e.g., all 26 buildings). The selection of the 20 buildings may be based, in part, on historical information regarding buildings previously visited by the owner of the mobile phone 1202. As yet another example, the 20 buildings may be established based on other criteria, such as day of week or month of the year. For example, if the day of the week is Friday, and if the owner of the mobile phone 1202 tends to visit a certain building on Fridays (e.g., the bank), then one of the example 20 buildings around which a geofence may be established is the bank building. Regardless of the precise method by which the example 20 buildings are selected, the example method generates a data set identifying the 20 buildings (or more precisely, identifying the 20 geofences) and sends the data set to the example mobile phone 1202. The mobile phone 1202, in turn, establishes the geofence boundaries within the mobile phone 1202 itself. When a geofence boundary is crossed by the mobile phone 1202, the mobile phone 1202 automatically contacts and downloads from the server 112 the data regarding the layout of the indoor area.

Consider, as an example, the mobile phone 1202 crosses the geofence 1204 associated with building 4. Once the geofence 1204 is crossed the mobile phone 1202, and in some cases before the mobile phone 1202 even enters the building, the mobile phone 1202 contacts the server 112. The server 112, in turn, downloads to the mobile phone 1202 the data regarding the layout of the indoor area for building 4. In yet still other cases, the server 112 further downloads the various parameters (e.g., P, A, and N) that the mobile phone 1202 may use for distance calculations within the building. Thus, once the mobile phone 1202 is within the example building 4, the mobile phone 1202 has already been provided data regarding navigation within the building.

It will be understood that if the mobile phone 1202 enters a building that is not surrounded by a geofence, the data regarding the layout of the indoor area, and parameters associated with distance calculations, will still be available to the mobile phone 1202. However, there may be a finite amount of time after entry of the building for the mobile phone 1202 to establish its location (e.g., by communicating with beacon devices in the building), send the request for data regarding the layout of the indoor area for the entered building to the server 112, and the server 112 providing that requested information. However, for every building entered around which a geofence has been established, the transition from outdoor navigation to indoor navigation can take place with little or no delay.

VII. Reliability Testing of Mobile Devices

In the context of reducing the spread of a contagion, whether by contact tracing for after-the-fact exposure tracing, or for avoiding areas having suspended micro-droplets of spittle, having a mobile device that is fully functioning and reliable may be an important component. For example, a mobile device that is malfunctioning may fail to record a contact, or may fail to provide alerts and/or routing information to avoid unsafe areas comprising suspended micro-droplets of spittle.

Referring again to FIGS. 1 and 2. In accordance with example embodiments, to ensure that mobile devices are functioning properly, the server 112 may periodically (e.g., once a minute, once an hour) request that each mobile device 102 perform an operational check. Responsive to the request, each mobile device 102 may perform the operational check and report the results to the server 112. The server 112 analyzes the results, and if the operational check fails, the server 112 sends an alert to the failed mobile device 102 regarding the failure. The failed mobile device 102, in turn, alerts the user (e.g., sound, display an alert on a display device) that the mobile device is experiencing issues and cannot be relied upon to accurately record contacts and/or to accurately avoid unsafe areas.

The operational check performed by each mobile device 102 at the request of the server 112 may take any suitable form. In example cases, the operational check checks for proper operation of some or all the various components of the mobile device 102, such as the main processor, the arithmetic logic unit (ALU), the memory, the short range transceivers, sensors, display device, camera, and the like.

In one example situation the operational check is a request for the mobile device 102 to perform a cryptograph operation whose resultant will only be correct if the ALU, memory, and related components are functioning properly. For example, the server 112 may provide a seed value of at least 250 bytes, and request the mobile device 102 to encrypt the seed value. Once complete, the mobile device 102 may send the encrypted value to the server 112 to be compared to the correct result as calculated by the server 112. In one specific example, the mobile device 102 encrypts the seed value provided by the server 112, the encryption with a private key of the mobile device 102. The mobile device sends the encrypted valued, along with the public key, to the server 112, and the server 112 decrypts the encrypted value with the public key. The server 112 considers the mobile device 102 as functioning properly when the decrypted value matches the seed value.

Other operational checks may also include a check to determined that the display device is operating properly as some mobile devices will fail to operate properly, or even shut down completely, if the display device is not fully functional (e.g., cracked). Yet still other operational checks may include testing sensors (e.g., inclinometers, accelerometers) for proper operation. For example, many sub-components will have an internal test routine that check their functionality and return a status code without requiring the user to do anything. Display device functionality, for example, may be tested by sending special, pre-designed codes to report on its operational health: '00' is sent to the display device, and the display device returns 'AA' to say it has dead pixels in region X,Y etc.

VIII. Example Computer System

Figure 13:
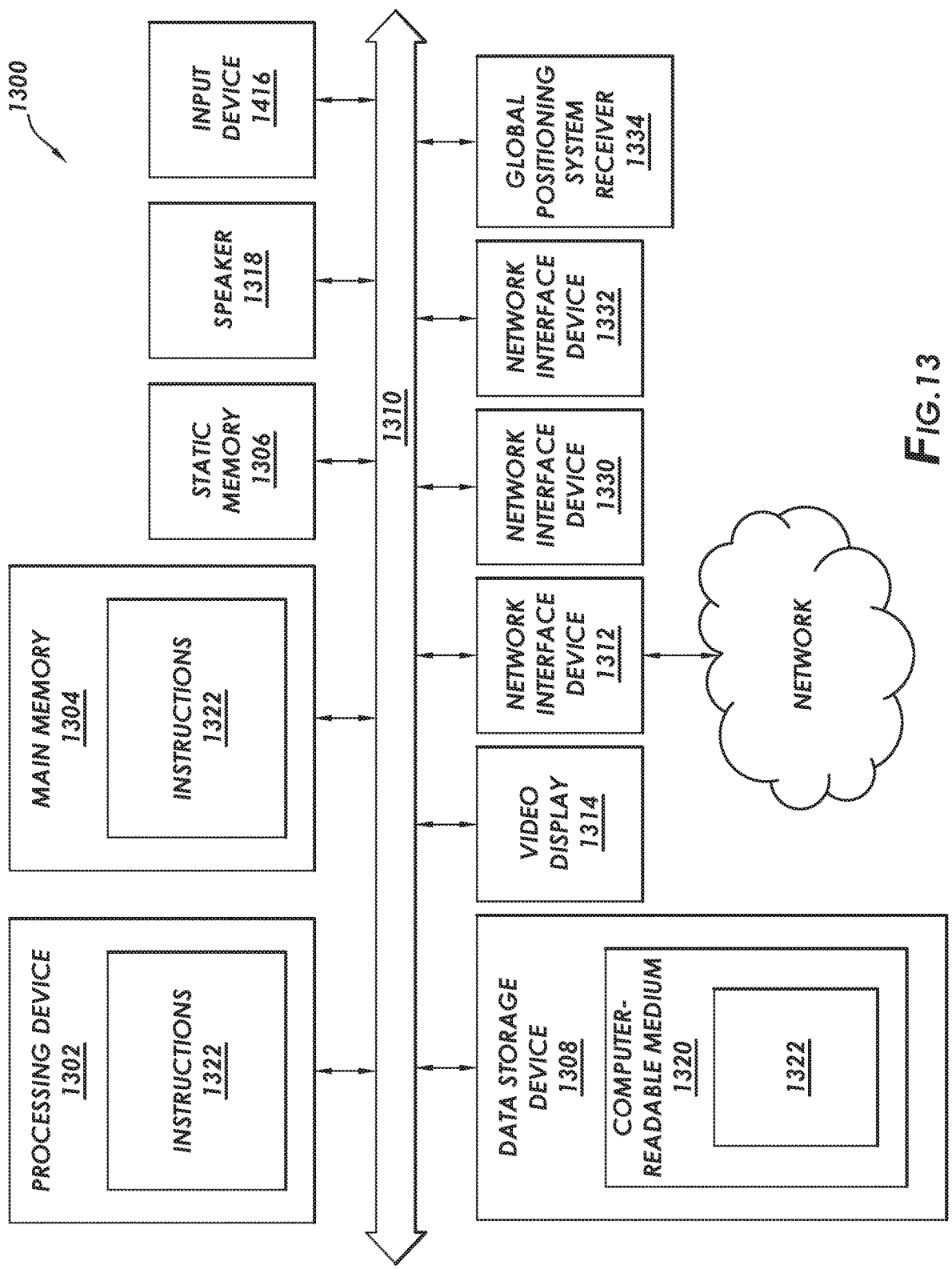
FIG. 13 shows a computer system in accordance with at least some embodiments.

FIG. 13 illustrates example computer system 1300 which can perform any one or more of the methods described herein, in accordance with one or more aspects of the present disclosure. In one example, the computer system 1300 may correspond to the mobile device(s) 102. In other cases, the computer system 1300 may correspond to server 112. The computer system 1300 may be capable of executing any application noted herein, including the contract tracing application (both peer-to-peer and location based), the navigation application, the monitoring application, and/or the geofencing application. The computer system 1300 may be connected (e.g., networked) to other computer systems in a local-area network (LAN), an intranet, an extranet, or the Internet. The computer system 1300 may operate in the capacity of the server 112 in a client-server network environment. In other cases, the computer system 1300 may be a smart phone, personal computer (PC), a tablet computer, a wearable (e.g., wristband, tag, smart watch), a set-top box (STB), a personal Digital Assistant (PDA), a camera, a video camera, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1300 includes a processing device 1302, a main memory 1304 (e.g., read-only memory (ROM), flash memory, dynamic random access memory (DRAM) such as synchronous DRAM (SDRAM)), a static memory 1306 (e.g., solid state drive (SSD), flash memory, static random access memory (SRAM)), and a data storage device 1308, which communicate with each other via a bus 1310.

Processing device 1302 represents one or more general-purpose processing devices such as a microprocessor, central processing unit, or the like. More particularly, the processing device 1302 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1302 may also be one or more special-purpose processing devices such as an application specific integrated circuit (ASIC), a field programmable gate array (FPGA), a digital signal processor (DSP), network processor, or the like. The processing device 1302 is configured to execute instructions for performing any of the operations and steps discussed herein.

The computer system 1300 may further include a network interface devices 1312, 1330, and 1332. The network interface device 1312 may be configured to communicate over long ranges via a wireless protocol (e.g., cellular, WiFi). The network interface device 1330 may be configured to communicate over medium ranges using point-to-point communication via a wireless protocol (e.g., BLE, UWB). The network interface device 1332 may be configured to communicate over short ranges using point-to-point communication via a wireless protocol (e.g., NFC, UWB). The computer system 1300 also may include a video display or display device 1314 (e.g., a liquid crystal display (LCD) or a cathode ray tube (CRT)), one or more input devices 1316 (e.g., a keyboard and/or a mouse), and one or more speakers 1318 (e.g., a speaker). In one illustrative example, the display device 1314 and the input device(s) 1316 may be combined into a single component or device (e.g., an LCD touch screen).

The computer system 1300 may further include a global positioning system (GPS) receiver 1334. The GPS receiver 1434 may be configured to receive signals from one or more GPS satellite and determines a distance from the satellites to obtain a latitude and longitude as location data. The GPS receiver 1334 may provide continuous real-time location data of the computer system 1300 to the processing device 1302.

The data storage device 1308 may include a computer-readable medium 1320 on which the instructions 1322 (e.g., implementing the actions of the server 112, or implementing contract tracing applications, the navigation applications, the monitoring applications, and/or the geofencing applications) embodying any one or more of the methodologies or functions described herein is stored. The instructions 1322 may also reside, completely or at least partially, within the main memory 1304 and/or within the processing device 1302 during execution thereof by the computer system 1300. As such, the main memory 1304 and the processing device 1302 also constitute computer-readable media. The instructions 1322 may further be transmitted or received over a network via the network interface device 1312.

While the computer-readable storage medium 1320 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A computer-implemented method to reduce spread of a contagion, the method comprising:
   creating, by a server system, an indication of suspended micro-droplets of spittle in an area of a building;
   receiving, by the server system, an indication that a mobile device is moving toward the area of the building; and
   sending, by the server system, an alert to the mobile device, the alert indicating that entry into the area of the building is not safe based on the indication of suspended micro-droplets of spittle.

2. The computer-implemented method of claim 1 wherein the creating the indication of suspended micro-droplets of spittle further comprises:
   receiving, by the server system, an indication of presence of a person within the area of the building;
   calculating, by the server system, a length of time the person spent within the area of the building; and
   generating, by the server system, the indication of suspended micro-droplets of spittle based on the indication of presence of the person and the length of time the person spent within the area.

3. The computer-implemented method of claim 1 wherein the creating the indication of suspended micro-droplets of spittle further comprises:
   receiving, by the server system, an indication of presence of a person within the area of the building;
   receiving, by the server system, an indication of departure of the person from the area of the building;
   calculating, by the server system, a time of presence of the person within the area of the building based on the indication of presence of the person within the area of the building and the indication of departure of the person from the area of the building;
   determining, by the server system, a time of absence of the person from the area of the building based on the indication of departure of the person from the area of the building; and
   generating, by the server system, the indication of suspended micro-droplets of spittle based on the time of presence and the time of absence.

4. The computer-implemented method of claim 3 wherein the generating further comprises generating the indication of the suspended micro-droplets of spittle based on the time of presence, the time of absence, and an environmental factor.

5. The computer-implemented method of claim 4 wherein the environmental factor is at least one selected from a group comprising: volume of the area of the building; airflow within the area of the building; and an intervening cleaning of the area of the building.

6. The computer-implemented method of claim 3 wherein the generating further comprises generating the indication of the suspended micro-droplets of spittle based on the time of presence, ambient sound during the time of presence, and the time of absence.

7. The computer-implemented method of claim 1:
   wherein sending the alert further comprises sending, by the server system a navigation pathway to a destination within the building, the navigation pathway excludes the area of the building; and
   further comprising providing, by the mobile device, the alert to a user of the mobile device.

8. The computer-implemented method of claim 1:
   wherein the area of the building is a workstation within the building, and the workstation is vacant;
   wherein the sending further comprises sending the alert to the mobile device, the alert indicating the workstation is not safe based on the indication of suspended micro-droplets of spittle.

9. The computer-implemented method of claim 1:
wherein the area of the building is a room within the building, and the room is vacant;
wherein the sending further comprises sending the alert to the mobile device, the alert indicating the room is not safe to enter based on the indication of suspended micro-droplets of spittle.

10. A server computer system comprising:
a processor;
a network interface coupled to the processor;
a memory coupled to the processor;
the memory stores a program that, when executed by the processor, causes the processor to:
create an indication of suspended micro-droplets of spittle in an area of a building, the building remote from the server computer system;
receive, by way of the network interface, an indication that a mobile device is moving toward the area of the building; and
send, by way of the network interface, an alert to the mobile device, the alert indicating that entry into the area of the building is not safe based on the indication of suspended micro-droplets of spittle.

11. The server computer system of claim 10 wherein when the processor creates the indication of suspended micro-droplets of spittle, the program further causes the processor to:
receive an indication of presence of a person within the area of the building;
calculate a length of time the person spent within the area of the building; and
generate the indication of suspended micro-droplets of spittle based on the indication of presence of the person and the length of time the person spent within the area.

12. The server computer system of claim 10 wherein when the processor creates the indication of suspended micro-droplets of spittle, the program further causes the processor to:
receive an indication of presence of a person within the area of the building;
receive an indication of departure of the person from the area of the building;
calculate a time of presence of the person within the area of the building based on the indication of presence and the indication of departure;
determine a time of absence of the person from the area of the building based on the indication of departure; and
generate the indication of suspended micro-droplets of spittle based on the time of presence and the time of absence.

13. The server computer system of claim 12 wherein when the processor generates the indication of suspended micro-droplets of spittle, the program further causes the processor to generate the indication of the suspended micro-droplets of spittle based on the time of presence, the time of absence, and an environmental factor.

14. The server computer system of claim 13 wherein the environmental factor is at least one selected from a group comprising: volume of the area of the building; airflow within the area of the building; and an intervening cleaning of the area of the building.

15. The server computer system of claim 12:
the program further causes the processor to receive an indication of ambient sound within the area of the building;
wherein when the processor generates the indication of suspended micro-droplets of spittle, the program further causes the processor to generate the indication of suspended micro-droplets of spittle based on the time of presence, the indication of ambient sound during the time of presence, and the time of absence.

16. The server computer system of claim 10:
wherein the area of the building is a workstation within the building, and the workstation is vacant;
wherein when the processor sends the alert, the program further causes the processor to send the alert to the mobile device, the alert indicating the work station is not safe based on the indication of suspended micro-droplets of spittle.

17. The server computer system of claim 10:
wherein the area of the building is a room within the building, and the room is vacant;
wherein when the processor sends the alert, the program further causes the processor to send the alert to the mobile device, the alert indicating the room is not safe to enter based on the indication of suspended micro-droplets of spittle.

* * * * *